(12) United States Patent
Baer et al.

(10) Patent No.: US 7,776,273 B2
(45) Date of Patent: Aug. 17, 2010

(54) LASER CAPTURE MICRODISSECTION (LCM) EXTRACTION DEVICE AND DEVICE CARRIER, AND METHOD FOR POST-LCM FLUID PROCESSING

(75) Inventors: Thomas M. Baer, Mountain View, CA (US); Robert H. Reamey, Palo Alto, CA (US); Keith E. Moravick, Palo Alto, CA (US); David F. Head, Los Gatos, CA (US); Bruce J. Richardson, Los Gatos, CA (US); Derrick A. Richardson, Pembroke Pines, FL (US)

(73) Assignee: Life Technologies Corporation, Carlsbad, CA (US)

( * ) Notice: Subject to any disclaimer, the term of this patent is extended or adjusted under 35 U.S.C. 154(b) by 206 days.

(21) Appl. No.: 09/844,187

(22) Filed: Apr. 26, 2001

(65) Prior Publication Data

US 2002/0001837 A1 Jan. 3, 2002

Related U.S. Application Data

(60) Provisional application No. 60/199,931, filed on Apr. 26, 2000.

(51) Int. Cl.
*B01L 3/00* (2006.01)
(52) U.S. Cl. .................. 422/102; 422/58; 422/68.1; 436/177
(58) Field of Classification Search ............ 436/177; 422/58, 68.1, 102

See application file for complete search history.

(56) References Cited

U.S. PATENT DOCUMENTS

| | | | | |
|---|---|---|---|---|
| 1,093,211 | A | | 4/1914 | Schulkoff .................. 220/789 |
| 2,649,245 | A | * | 8/1953 | Silverstolpe ................. 494/10 |
| 2,801,568 | A | | 8/1957 | Dakin ........................... 88/40 |
| 3,680,947 | A | | 8/1972 | Wanesky ..................... 350/81 |
| 3,799,426 | A | * | 3/1974 | Pates et al. ................... 229/4.5 |
| 3,940,250 | A | | 2/1976 | Plakas et al. ................. 23/230 |
| 4,039,247 | A | | 8/1977 | Lawman ...................... 350/95 |
| 4,149,803 | A | | 4/1979 | Litz ............................ 356/244 |
| 4,303,866 | A | | 12/1981 | Porro et al. ................ 250/442 |
| 4,310,488 | A | * | 1/1982 | Rahm et al. ................ 422/102 |

(Continued)

FOREIGN PATENT DOCUMENTS

CH 566 015 8/1975

(Continued)

OTHER PUBLICATIONS

Bonner, Robert F. et al. (Nov. 21, 1997). "Laser capture microdissection: Molecular analysis of tissue," *Science* 278:1481-1482.

(Continued)

*Primary Examiner*—Jan M Ludlow
(74) *Attorney, Agent, or Firm*—Fish & Richardson P.C.

(57) ABSTRACT

The present invention generally discloses an extraction system that provides a locale for fluid processing and extraction on a post-microcapture transfer film. The extraction system includes a transfer film carrier and an extraction device forming a reservoir. The extraction system selectively excludes regions of the transfer film from the reservoir to advantageously reduce contamination due to matter adhered to the transfer film by non-specific transfer.

8 Claims, 18 Drawing Sheets

U.S. PATENT DOCUMENTS

| | | | |
|---|---|---|---|
| 4,341,635 A * | 7/1982 | Golias | 210/656 |
| 4,467,915 A | 8/1984 | Snyder et al. | 206/219 |
| 4,632,672 A * | 12/1986 | Kvitrud | 604/222 |
| 4,807,984 A | 2/1989 | Kurimura et al. | 350/529 |
| 4,834,946 A | 5/1989 | Levin | 422/101 |
| 4,920,053 A | 4/1990 | Inoue et al. | |
| 5,063,025 A * | 11/1991 | Ito | 422/100 |
| 5,103,338 A | 4/1992 | Crowley et al. | |
| 5,158,895 A | 10/1992 | Ashihara et al. | 436/526 |
| 5,188,963 A | 2/1993 | Stapleton | 435/299 |
| 5,192,503 A | 3/1993 | McGrath et al. | |
| 5,217,768 A | 6/1993 | Walters et al. | 428/35.8 |
| 5,246,866 A | 9/1993 | Nasu et al. | |
| 5,280,384 A | 1/1994 | Shibasaki | |
| 5,281,516 A | 1/1994 | Stapleton et al. | 435/3 |
| 5,288,996 A | 2/1994 | Betzig et al. | 250/227.26 |
| 5,346,672 A | 9/1994 | Stapleton et al. | 422/102 |
| 5,382,511 A | 1/1995 | Stapleton | 435/6 |
| 5,412,087 A | 5/1995 | McGall et al. | 536/24.3 |
| 5,412,513 A | 5/1995 | Nederlof | 359/393 |
| 5,415,994 A | 5/1995 | Imrich et al. | 435/5 |
| 5,427,948 A | 6/1995 | Diers | 435/312 |
| 5,436,129 A | 7/1995 | Stapleton | 435/6 |
| 5,439,650 A | 8/1995 | Tsugita et al. | 422/108 |
| 5,451,500 A | 9/1995 | Stapleton | 435/6 |
| 5,486,335 A | 1/1996 | Wilding et al. | 422/55 |
| 5,494,646 A | 2/1996 | Seymour | |
| 5,504,366 A | 4/1996 | Weiss et al. | |
| 5,513,768 A | 5/1996 | Smith | |
| 5,516,490 A | 5/1996 | Sanadi | 422/101 |
| 5,532,128 A | 7/1996 | Eggers et al. | |
| 5,538,849 A | 7/1996 | Uematsu et al. | |
| 5,545,531 A | 8/1996 | Rava et al. | |
| 5,559,329 A | 9/1996 | Joseph et al. | |
| 5,598,888 A | 2/1997 | Sullivan et al. | 165/263 |
| 5,619,035 A | 4/1997 | Weiss et al. | |
| 5,624,554 A | 4/1997 | Faulkner et al. | 210/232 |
| 5,627,041 A | 5/1997 | Shartle | 435/7.24 |
| 5,639,428 A | 6/1997 | Cottingham | |
| 5,658,531 A * | 8/1997 | Cope et al. | 422/58 |
| 5,677,197 A | 10/1997 | Gordon et al. | |
| 5,681,741 A | 10/1997 | Atwood et al. | 435/287.2 |
| 5,681,742 A | 10/1997 | MersKelly et al. | 435/288.1 |
| RE35,716 E | 1/1998 | Stapleton et al. | 435/3 |
| 5,741,710 A | 4/1998 | Ek | 436/73 |
| 5,756,049 A | 5/1998 | Brayton | |
| 5,763,191 A | 6/1998 | Knoll et al. | 435/7.1 |
| 5,798,215 A | 8/1998 | Cathey et al. | |
| 5,843,644 A | 12/1998 | Liotta et al. | |
| 5,843,657 A | 12/1998 | Liotta et al. | 435/6 |
| 5,843,767 A | 12/1998 | Beattie | |
| 5,859,699 A | 1/1999 | Baer et al. | |
| 5,860,937 A | 1/1999 | Cohen | |
| 5,874,219 A | 2/1999 | Rava et al. | |
| 5,879,625 A | 3/1999 | Roslaniec et al. | |
| 5,885,531 A | 3/1999 | Heffelfinger et al. | 422/82.05 |
| 5,885,837 A | 3/1999 | Winkler et al. | 435/91.1 |
| 5,891,630 A | 4/1999 | Eggers et al. | |
| 5,912,134 A | 6/1999 | Shartle | 435/7.24 |
| 5,936,858 A | 8/1999 | Arai | 364/150 |
| 5,981,733 A | 11/1999 | Gamble et al. | 536/25.3 |
| 5,985,085 A | 11/1999 | Baer et al. | |
| 6,043,080 A | 3/2000 | Lipshutz et al. | 435/287.2 |
| 6,057,165 A * | 5/2000 | Mansour | 436/518 |
| 6,084,237 A | 7/2000 | Troster et al. | 250/288 |
| 6,084,660 A | 7/2000 | Shartle | 356/39 |
| 6,114,122 A | 9/2000 | Besemer et al. | 435/6 |
| 6,157,446 A | 12/2000 | Baer et al. | |
| 6,159,727 A | 12/2000 | Bochkariov | 435/287.2 |
| 6,184,973 B1 * | 2/2001 | Baer et al. | 356/36 |
| 6,204,030 B1 | 3/2001 | Liotta et al. | |
| 6,215,550 B1 * | 4/2001 | Baer et al. | 356/36 |
| 6,221,655 B1 | 4/2001 | Fung et al. | 435/288.1 |
| 6,238,910 B1 | 5/2001 | Custance et al. | 435/287.2 |
| 6,258,593 B1 | 7/2001 | Schembri | 435/287.2 |
| 6,277,648 B1 | 8/2001 | Colpan | |
| 6,309,875 B1 | 10/2001 | Gordon | 435/287.2 |
| 6,469,779 B2 * | 10/2002 | Baer et al. | 356/36 |
| 6,512,576 B1 * | 1/2003 | Baer et al. | 356/36 |
| 6,528,248 B2 * | 3/2003 | Lossing et al. | 435/4 |
| 6,639,657 B2 * | 10/2003 | Baer et al. | 356/36 |
| 6,697,149 B2 * | 2/2004 | Baer et al. | 356/36 |
| 6,720,191 B1 * | 4/2004 | Goldstein et al. | 436/174 |
| 7,075,640 B2 * | 7/2006 | Baer et al. | 356/244 |
| 2001/0046700 A1 | 11/2001 | Custance et al. | 435/287.2 |

FOREIGN PATENT DOCUMENTS

| | | |
|---|---|---|
| DE | 196 03 996 A1 | 2/1996 |
| EP | 0 611 598 A2 | 8/1994 |
| EP | 0 388 168 B1 | 12/1994 |
| WO | WO 91/07683 | 5/1991 |
| WO | WO 93/11221 | 6/1993 |
| WO | WO 93/19207 | 9/1993 |
| WO | WO 95/23960 | 9/1995 |
| WO | WO 95/30919 | 11/1995 |
| WO | WO 96/40435 | 12/1996 |
| WO | WO 97/13838 | 4/1997 |
| WO | WO 98/35215 | 8/1998 |
| WO | WO 98/35216 | 8/1998 |
| WO | WO 99/17094 | 4/1999 |
| WO | WO99/17094 * | 4/1999 |
| WO | WO 00/05587 | 2/2000 |
| WO | WO 00/05587 A2 | 2/2000 |
| WO | WO 00/05587 A3 | 2/2000 |
| WO | WO 00/06992 | 2/2000 |
| WO | WO 01/30489 A2 | 5/2001 |
| WO | WO 01/43871 A2 | 6/2001 |
| WO | WO 02/37159 A2 | 5/2002 |

OTHER PUBLICATIONS

Brignole, Ed (Nov./Dec. 2000). "Laser-capture microdissection," *Modern Drug Discovery* pp. 1-3.

Chu, Samuel S. et al. (Apr. 2000). "Laser capture microdissection: Applications in cancer research," *Biomedical Products* pp. 1-3.

Chui, Glennda (Jun. 1, 1999). "The ecosystems within" Section F, Science & Technology *San Jose Mercury News* pp. 1-5.

Emmert-Buck, Michael R. et al. (Nov. 8, 1996). "Laser capture microdissection," *Science* 274:998-1001.

Goldsworthy, Susan M. et al. (1999). "Effects of fixation on RNA extraction and amplification from laser capture microdissected tissue" *Molecular Carcinogenesis* 25:86-91.

Isenberg, G. et al. (1976). "Cell surgery by laser micro-dissection: a preparative method," *J. Microsc.* 107(Pt 1):19-24.

Meier-Ruge, W. et al. (1976). "The laser in the Lowry technique for microdissection of freeze-dried tissue slices," *Histochemical Journal* 8:387-401.

Relman, David A. (May 21, 1999). "The search for unrecognized pathogens," *Science* 284:1-3.

Schindler, M. et al. (Jul. 1985). "Automated analysis & survival selection of anchorage-dependent cells under normal growth conditions," *Cytometry* 6(4):368-374.

Schindler, Melvin (Aug. 1998). "Select, microdissect & eject," *Nature Biotechnology* 16:719-720.

Schütze, Karin and Lahr, Georgia (Aug. 1998). "Identification of expressed genes by laser-mediated manipulation of single cells," *Nature Biotechnology* 16(8):737-742.

Simone, Nicole L. et al. (1998). "Laser capture microdissection; opening the microscopic frontier to molecular analysis," *Trends Genet.* 14(7):272-276.

Ashkin, A. & Dziedzic J.M. (1989) "Internal Cell Manipulation Using Infrared Laser Traps" Pro.Nat. Acad. Sc. 86:20:7914-7918.

Bonner, R.F., et al. (1997) "Laser Capture Microdissection: Molecular Analysis of Tissue", Amer. Assoc. Advanc. of Sci., 278:1481-1843.

Emmert-Buck, Michael R. et al., (1996) "Laser Capture Microdissection", *Science*, 274:998-1001.

Friend, T. (Oct. 29, 2001) "Getting up close to cancer genes Microdissection breakthrough lets scientists isolate those involved in tumor growth." USA Today.com, http://pqasb.pqarchiver.coni/USAToday/main/doc/.

Geduspan, Jane S., & Solursh, Michael (1992) "A Growth-Promoting Influence from the Mesonephros During Limb Outgrowth," *Developmental Biology*, 151:242-250.

Jimenez, C. R., et al., (1994) "Neuropeptide Expression and Processing as Revealed by Direct Matrix-Assisted Laser Desorption Ionization Mass Spectrometry of Single Neurons", *Journal of Neurochemistry*, 62:404-707.

Kubo, Y., et al., (1995) "Early Detection of Knudson's Two-hits in Preneoplastic Renal Cells of the Eker Rat Model by the Laser Microdissection Procedure," *Cancer Res.* 55:975-1197.

Meier-Ruge, W. et al., (1976) "The laser in the Lowry Technique for Microdissection of Freeze-dried Tissue Slices", *Histochemical J.*, pp. 8:387-401.

Schutze, Karin & Lahr, Georgia (Aug. 1998) "Identification of Expressed Genes by Laser-Mediated Manipulation of Single Cells", *Nature Biotechnology*, 16:737-742.

Schindler, M., et al., (Jul. 1985) "Automated Analysis and Survival Selection of Anchorage-Dependent Cells Under Normal Growth Conditions", *Cytometry* 6:368-374.

Schindler, M. (Aug. 1998) "Select, Microdissect, and Eject", *Nature Biotechnology* 16:719-720.

Veigel, C., et al. (1993) "New Cell Biological Applications of the Laser Microbeam Technique: the Microdissection and Skinning of Muscle Fibers and the Perforation and Fusion of Sarcolemma Vesicles", *European Journal of Cell Biology* 63:1:140-148.

\* cited by examiner

LASER CAPTURE MICRODISSECTION (LCM) EXTRACTION DEVICE AND DEVICE CARRIER, AND METHOD FOR POST-LCM FLUID PROCESSING

CROSS-REFERENCE TO RELATED APPLICATIONS

This application claims priority to U.S. Provisional Patent Application Ser. No. 60/199,931, entitled "LASER CAPTURE MICRODISSECTION (LCM) EXTRACTION DEVICE AND DEVICE CARRIER, AND METHOD FOR POST-LCM FLUID PROCESSING", filed Apr. 26, 2000.

TECHNICAL FIELD

This invention relates generally to laser micro-capture, in particular, to an extraction device and method for post-micro-capture fluid processing.

BACKGROUND

Diseases such as cancer have long been identified by examining tissue biopsies to identify unusual cells. The problem has been that there has been no satisfactory prior-art method to capture a single cell or multiple cells of interest from the surrounding tissue. Currently, investigators must attempt to manually extract, or microdissect, cells of interest either by attempting to mechanically isolate them with a manual tool or through a convoluted process of isolating and culturing the cells. Most investigators consider both approaches to be tedious, time-consuming, and inefficient.

A new technique has been developed which can extract a single cell or a small cluster of cells from a tissue sample in a matter of seconds. The technique is called laser capture microdissection (LCM). In laser capture microdissection, the operator looks through a microscope at a biological specimen such as a tissue biopsy section mounted on a standard glass histopathology slide, which typically contains a variety of cell types. A transfer film is placed over the tissue biopsy section such that the transfer film may or may not contact the tissue. Upon identifying a cell or a group of cells of interest within the tissue section with the aid of a microscope, for example, the operator generates a pulse from a laser. The laser pulse causes localized heating of the thermoplastic film, imparting to it an adhesive property, and thereby, activating the film. The target cells then stick to the localized adhesive area of the thermoplastic film directly above them. Upon removal of the film from the biopsy tissue, the selected cells or sections of tissue are transferred along with the film. Because of the small diameter of the laser beam, extremely small cell clusters or single cells may be microdissected from a tissue section. Biomolecules are then extracted from the transfer film for subsequent analysis.

By taking only these target cells directly from the tissue sample, scientists can immediately analyze the DNA, RNA, proteins, or other biomolecules in order to characterize the activity of the target cells using other research tools. Such procedures as polymerase chain reaction amplification of DNA and RNA, and enzyme recovery from the tissue sample are typically employed.

Laser capture microdissection has successfully extracted cells in many types of tissues. These include kidney glomeruli, in situ breast carcinoma, atypical ductal hyperplasia of the breast, prostatic interepithielial neoplasia, and lymphoid follicles. The direct access to cells provided by laser micro-capture will likely lead to a revolution in the understanding of the molecular basis of cancer and other diseases, helping to lay the groundwork for earlier and more precise disease detection.

Another likely role for the technique is in recording the patterns of gene expression in various cell types, an emerging issue in medical research. For instance, the National Cancer Institute's Cancer Genome Anatomy Project (CGAP) is attempting to define the patterns of gene expression in normal, precancerous, and malignant cells. In projects such as CGAP, laser capture microdissection is a valuable tool for procuring pure cell samples from tissue samples.

The LCM technique is generally described in the published article: Laser Capture Microdissection, Science, Volume 274, Number 5289, Issue 8, pp 998-1001, published in 1996, the entire contents of which are incorporated herein by reference. The purpose of the LCM technique is to provide a simple method for the procurement of selected human cells from a heterogeneous population contained on a typical histopathology biopsy slide.

A typical biological specimen is a tissue biopsy sample consisting of a 5 to 10 micron slice of tissue that is placed on a glass microscope slide using fixation and staining techniques well known in the field of pathology. This tissue slice is a cross section of the body organ that is being studied. The tissue consists of a variety of different types of cells. Often a pathologist desires to remove only a particular cell type or a small portion of the tissue for further analysis. Another typical biological specimen is a layer of cells coated from a liquid suspension.

Laser micro-capture employs a transfer film that is placed over the tissue sample such that it may or may not contact the tissue sample. In contact micro-capture, the transfer film contacts the tissue sample prior to activation by the laser pulse. Due to the friable nature of tissue sections, loose material (whole cell or macromolecular) is likely to adhere to the transfer film even though it was not targeted by the laser. Hence, non-specific transfer of material results. If these non-targeted portions are transferred to the reagent vessel for subsequent analysis, they will be digested by the reagents and contaminate the targeted portions in the sample. Therefore, it is important to prevent the non-targeted portions such as loosely bound tissue areas from contacting the transfer film. Reducing the incidents of non-specific transfer is one aspect of the present invention.

One way of reducing the problem of non-specific transfer is to provide a non-stick barrier layer as described in co-pending application U.S. Ser. No. 09/562,495 filed on May 1, 2000, which is, in its entirety, incorporated herein by reference. Another way of reducing non-specific transfer, for example, is non-contact LCM. In non-contact LCM, the transfer film is offset or distanced a few microns from the tissue sample as described in co-pending application U.S. Ser. No. 08/984,979 filed on Dec. 4, 1997, which is, in its entirety, incorporated herein by reference. As described in this co-pending application, stand-offs are employed to distance or offset the transfer film a few microns from the tissue sample. Distancing the transfer film from the tissue sample reduces incidents of non-specific transfer. However, if stand-offs are employed, non-specific transfer of material is generally confined to the stand-off portions that generally contact the tissue sample in order to space the transfer film away from the tissue sample. Since the stand-off portions are loci for non-specific transfer, it is desirable to prevent the contamination of targeted cells with non-specific material from the stand-off portions. Contamination is particularly possible when extraction fluids such as buffer is introduced to contact the desired material on the transfer film for extraction of particular biomolecules and their subsequent analysis. If buffer is brought into contact with non-specific material on the transfer film such as the material on stand-off portions, that material will be digested along with the targeted material and thereby contaminate the analysis. Therefore, it is desirable to prevent the incorporation of non-specific material. The present invention is aimed at reducing non-specific transfer of material that would contaminate the analysis. Also, the present invention facilitates the introduction of extraction fluids for the post-LCM extraction of desired biomolecules.

SUMMARY OF INVENTION

In accordance with one aspect of the invention, there is provided an extraction device for mating with a carrier comprising a carrier-receiving portion at a first end and a conduit interconnected to the carrier-receiving portion. The conduit extends between the carrier-receiving portion and a second end. The carrier-receiving portion is adapted to receive a carrier such that a reservoir is formed.

In accordance with another aspect of the invention, there is provided an extraction device for mating with a carrier comprising a carrier-receiving portion at a first end and a conduit interconnected to the carrier-receiving portion. The conduit extends between the carrier-receiving portion and a second end. The carrier-receiving portion is adapted to receive a carrier having a transfer film such that a reservoir is formed. The reservoir is formed such that a portion of the transfer film is disposed within the reservoir.

In accordance with another aspect of the invention, there is provided an extraction device for mating with a carrier comprising a carrier-receiving portion at a first end and a conduit interconnected to the carrier-receiving portion. The carrier-receiving portion is adapted to receive a carrier and to form a reservoir and further adapted to selectively cover at least a portion of the carrier.

In accordance with another aspect of the invention, there is provided an extraction system comprising a carrier having a transfer film and an extraction device. The extraction device is removably coupled to the carrier. The extraction device comprises a carrier-receiving portion interconnected to at least one conduit. The carrier-receiving portion being adapted to receive the carrier such that a reservoir is formed.

In accordance with another aspect of the invention, there is provided an extraction device for mating with a carrier comprising a carrier-receiving portion at a first end. The carrier-receiving portion includes a shoulder and at least one flange that extends from the shoulder. The carrier-receiving portion further includes a landing portion having a landing surface that defines an inner opening. The extraction device further includes a conduit interconnected to the carrier-receiving portion at the inner opening. The conduit extends between the carrier-receiving portion and a second end. The carrier-receiving portion is adapted to receive a carrier and to form a reservoir by the carrier contacting the landing portion.

In accordance with yet another aspect of the invention, there is provided an extraction device for mating with a carrier comprising a carrier-receiving portion at a first end. The carrier-receiving portion includes an inner surface, a recess, and a landing portion. The recess is interconnected with the inner surface and the landing portion. The landing portion forms a landing rim that is raised from the recess. The landing rim defines an inner opening. The extraction device further includes a conduit interconnected to the carrier-receiving portion at the inner opening. The conduit extends between the carrier-receiving portion and a second end. The carrier-receiving portion is adapted to receive a carrier and to form a reservoir by the carrier contacting the landing rim.

In accordance with another aspect of the invention, there is provided an extraction device for mating with a carrier comprising a carrier-receiving portion at a first end. The carrier-receiving portion includes an inner surface, a landing portion, and a reservoir-forming surface. The landing portion is interconnected with the inner surface and the reservoir-forming surface. The reservoir-forming surface is encompassed by the landing portion. The extraction device further includes at least one conduit interconnected to the carrier-receiving portion. The conduit extends between the reservoir-forming surface and a second end. The carrier-receiving portion is adapted to receive a carrier and to form a reservoir by the carrier contacting the landing portion.

In accordance with another aspect of the invention, there is provided an extraction device for mating with a carrier comprising a first surface, a second surface, an outer surface, and an inner surface. The first and second surfaces are interconnected by the outer and inner surfaces. The inner surface defines a conduit extending between the first surface and the second surface. A reservoir is formed by the carrier being joined to the extraction device at the first surface such that the reservoir is defined by the carrier and the conduit.

In accordance with another aspect of the invention, there is provided an extraction device delivery system comprising a base and a locator connected to the base. The locator includes at least one aperture adapted to receive at least one extraction device.

In accordance with another aspect of the invention, a method for extracting matter on a carrier is provided. The method includes providing a carrier having a transfer film. Matter is transferred to the transfer film. An extraction device is provided. The extraction device is mated to the carrier. A reservoir is formed with the transfer film and fluid is provided into the reservoir to extract matter from the transfer film. The fluid is removed from the reservoir.

In accordance with another aspect of the invention, a method of delivering at least one extraction device is provided. The method includes the step of providing an extraction device delivery system comprising a base and a locator connected to the base. The locator includes at least one aperture adapted to receive at least one extraction device. At least one extraction device is provided and disposed within the at least one aperture. A carrier having a transfer film is provided. The carrier is passed through the locator such that the transfer film contacts the at least one extraction device. The carrier is adhered to the extraction device to form a carrier-extraction device combination. The carrier-extraction device combination is removed.

In accordance with another aspect of the invention there is provided a method for extraction. The method includes the step of transferring matter to a carrier by microcapture. An extraction device having a carrier-receiving portion and at least one conduit is provided. The carrier is inserted into the carrier-receiving portion. A reservoir is formed comprising at least one surface of the extraction device and at least one surface of the carrier. The reservoir is interconnected to the at least one conduit. Fluid is introduced fluid into the reservoir via the at least one conduit to extract matter on the transfer film and the fluid is removed.

BRIEF DESCRIPTION OF THE DRAWINGS

The foregoing and other advantages of the invention will become apparent upon reading the following detailed description and upon reference to the drawings in which.

Figure 1:
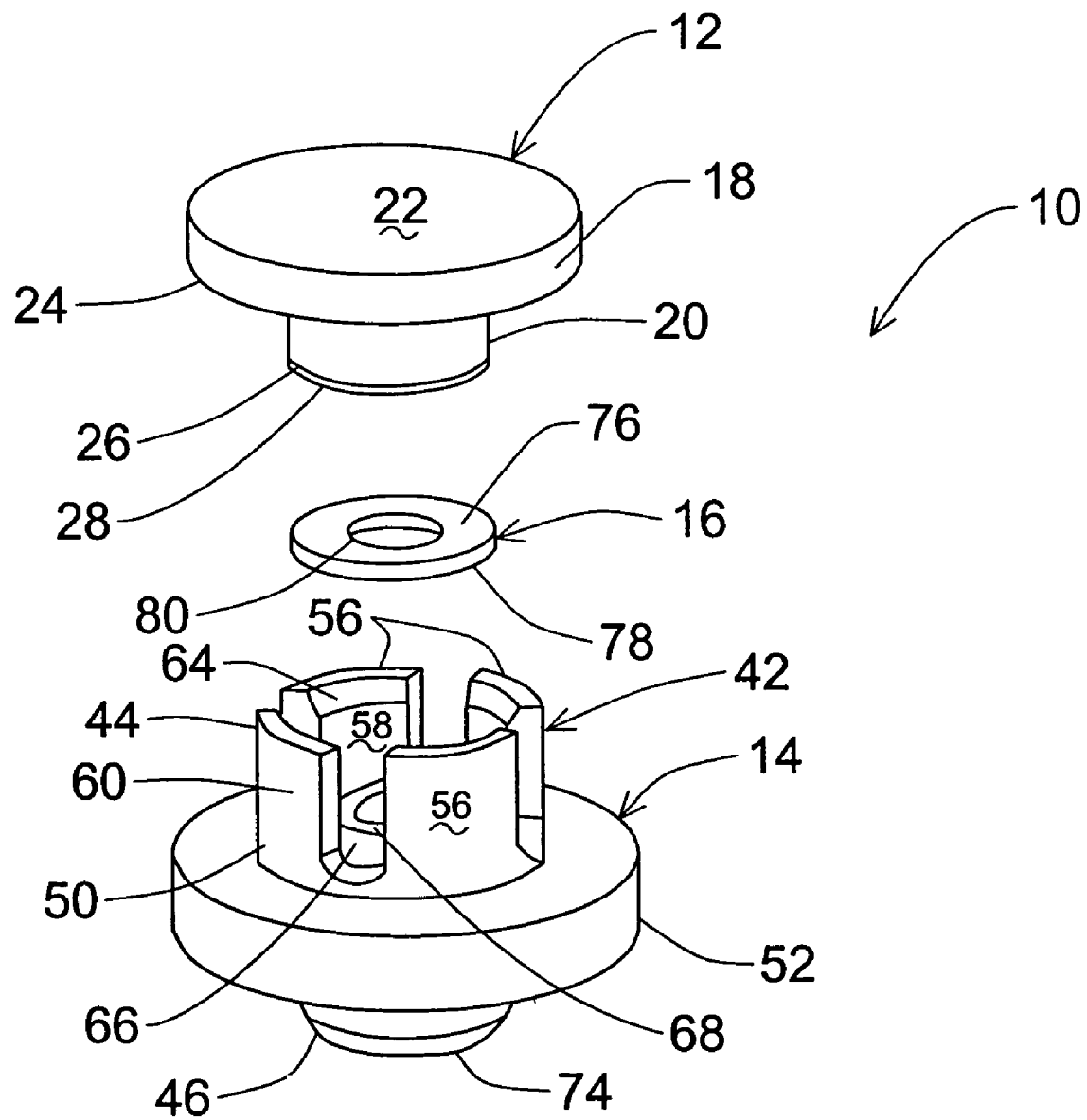
FIG. 1 is an exploded perspective view of an extraction system comprising a carrier, a gasket and an extraction device of the present invention.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION

This application claims priority to U.S. Provisional Patent Application Serial No. 60/199,931, entitled "LASER CAPTURE MICRODISSECTION (LCM) EXTRACTION DEVICE AND DEVICE CARRIER, AND METHOD FOR POST-LCM FLUID PROCESSING", filed Apr. 26, 2000, which is incorporated herein by reference in its entirety.

Turning now to the drawings and referring initially to FIG. 1, there is depicted an exploded view of an extraction system 10 comprising a carrier 12, an extraction device 14, and a gasket 16. The carrier 12 is adapted to be removably coupled to the extraction device 14 such that when the carrier 12 is coupled to the extraction device 14, the gasket 16 is engaged.

Figure 2:
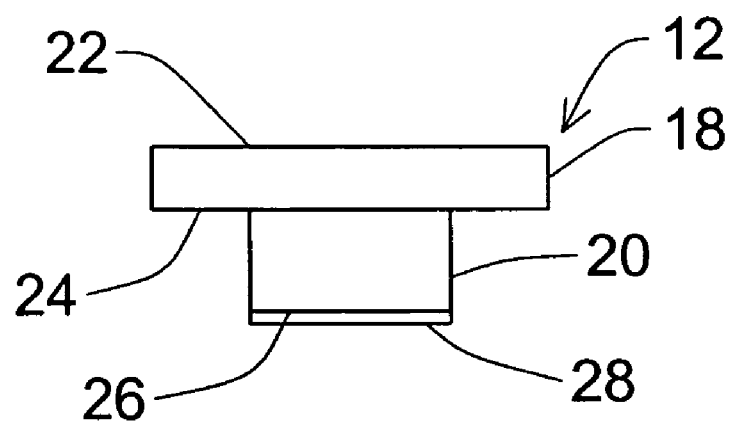
FIG. 2 is a side view of a carrier.
Figure 3:
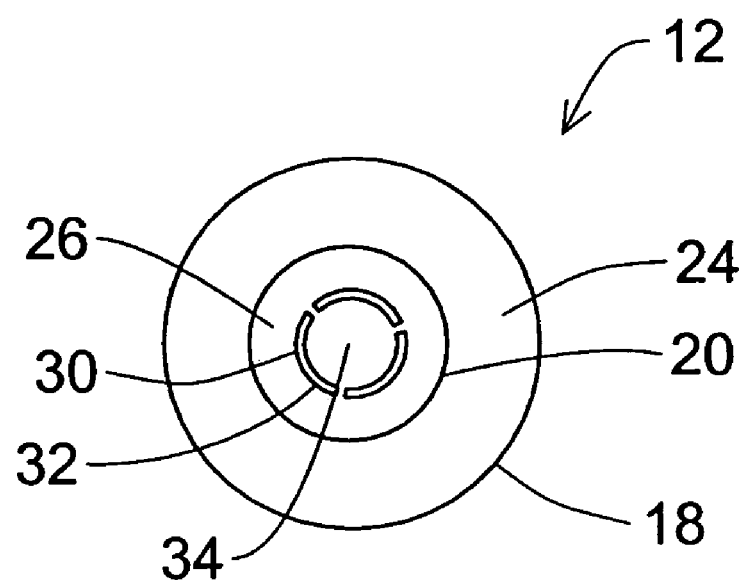
FIG. 3 is a bottom view of a carrier.

Referring to FIGS. 1-3, the carrier 12 is made from an inert and, preferably, transparent plastic such as acrylic (polymethyl methacrylate). Although the carrier 12 is shown having a cap-like shape, the carrier 12 and its configuration are not limited to this geometry. The carrier 12 includes an upper portion 18 and a lower portion 20. The upper portion 18 includes a top surface 22 and a shoulder 24. The lower portion 20 includes a substrate surface 26 to which a transfer film 28 is coupled.

The transfer film 28 is adapted for absorbing energy delivered by a laser pulse or multiple laser pulses of the same or different energy wavelengths. The transfer film 28 is further adapted for expanding and adhering to the target cells. Typically, when activated by a laser pulse, the transfer film 28 absorbs energy, expands, and adheres to a sample to be captured.

A variety of thermoplastic polymer films are used as heat activated adhesives that are suitable for the transfer film 28. Generally, it is preferred to use a polymer film having a high melt index range such as greater than 100 dg/min so that it is activatable at lower temperatures to avoid damage to or change in the nature of the tissue sample 28. Therefore, it is important that the temperature of the portion of the transfer film contacting the sample is below approximately 100° C., preferably below approximately 80° C., and more preferably below approximately 60° C. The melt index is generally measured according to ASTM D1238 in which a sample of polymeric material is melted isothermally in a heated chamber and then pushed out of a capillary orifice under a fixed load. The amount of extruded material is measured over time and the melt flow rate (index) is determined in decigrams/minute. The invention is not limited to transfer films comprising heat activated adhesive materials. Pressure sensitive adhesives may be employed as well as other materials and types of transfer films 28.

According to one variation, the carrier 12 includes at least one extending feature 30. Extending features 30 include at least one stand-off portion or spacer 32. Extending features 30 are described in U.S. Pat. No. 5,985,085 issued on Nov. 16, 1999 to Baer et al. and in co-pending U.S. application Ser. No. 08/984,979 filed on Dec. 4, 1997 both of which are incorporated herein by reference in their entirety.

The stand-off portions 32 project away from the substrate surface 26 a distance of approximately 1.0 μm to 12.0 μm in order to distance the transfer film 28 from a tissue sample. Three curved stand-off portions 32, each having a substantially rectangular cross-section to encompass an adhesion zone 34 are shown in FIG. 3. The cross-section of the stand-off portion 32 may be of any shape and any number of stand-off portions 32 may be employed encompassing an adhesion zone 34 that is of any shape or size. For example, a single stand-off portion 32 may encompasses the perimeter of the substrate surface 26.

The extending features 30 can be integrally formed with the transfer film 28 or, for example, be fabricated by hot cast molding the transfer film 28 against a mold that has complimentary shapes of the extending features 30. Alternatively, the extending features 30 are not formed in the transfer film 28, but are formed in the material of the lower portion 30 of the carrier 12 using methods well-known in the art.

Figure 4:
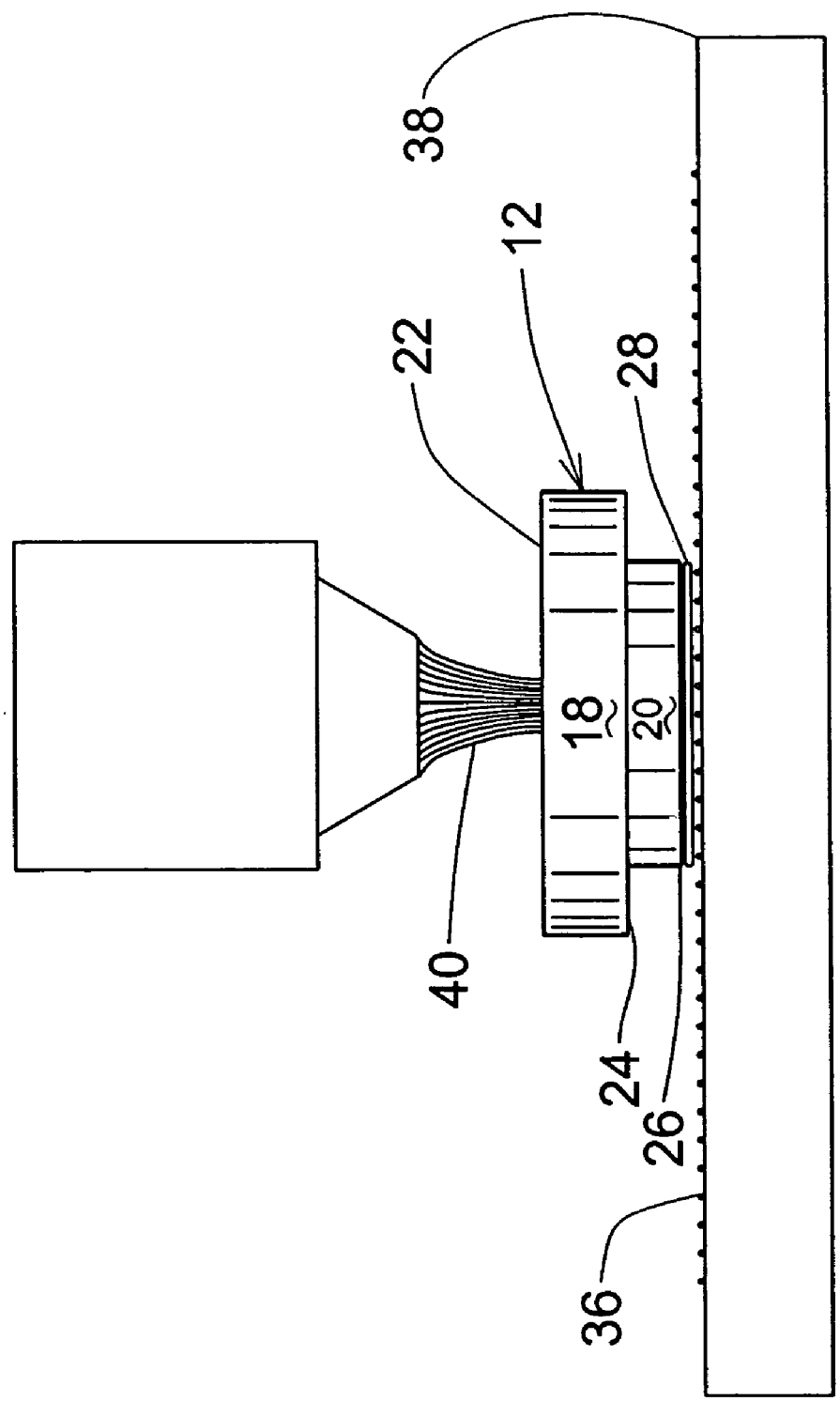
FIG. 4 is a side view of a carrier located above a sample on a slide and a laser pulse.
Figure 5:
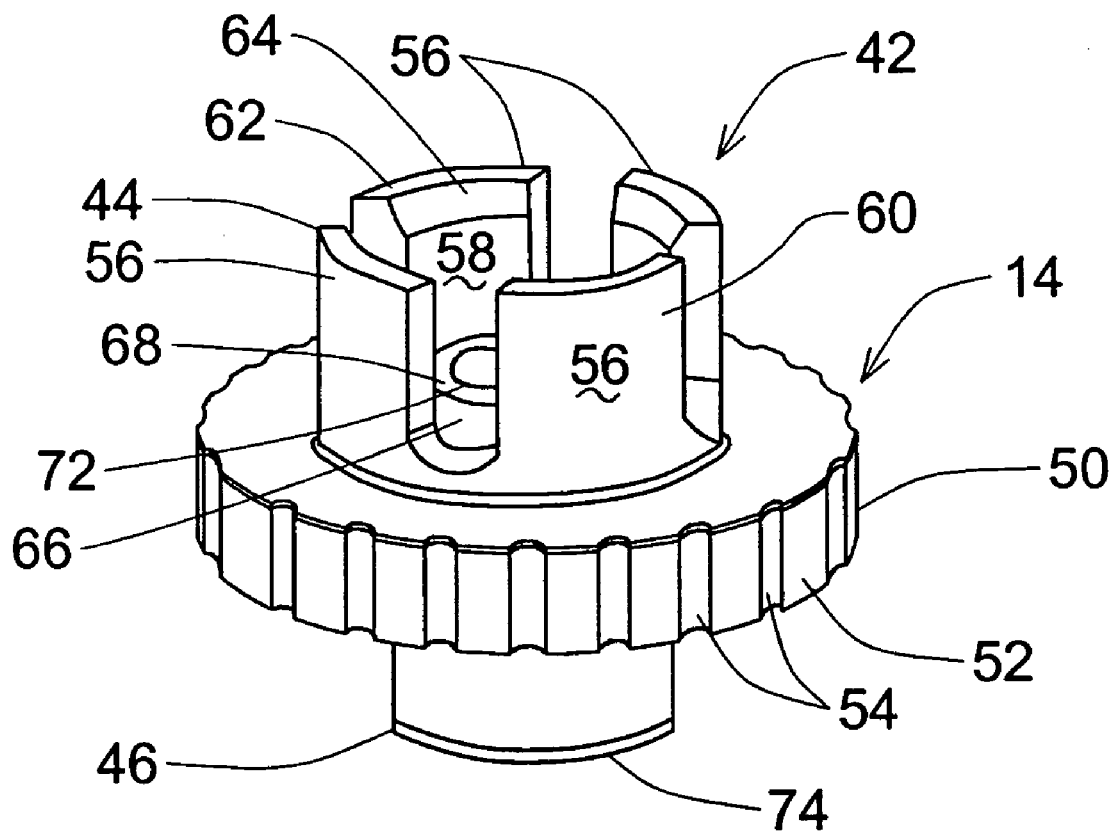
FIG. 5 is a perspective view of an extraction device of the present invention.

Referring now to FIG. 4, in laser capture microdissection, the operator looks through a microscope at a biological specimen 36 such as a tissue biopsy section mounted on a standard glass histopathology slide 38, which typically contains a variety of cell types. A transfer film 28 is placed over the tissue biopsy section 36 such that the transfer film 28 may or may not contact the tissue 36. Upon identifying a cell or a group of cells of interest within the tissue section 36 with the aid of a microscope, for example, the operator generates a pulse from a laser. The laser pulse 40 causes localized heating of the thermoplastic film, imparting to it an adhesive property, and thereby, activating the transfer film 28. The target cells then stick to the localized adhesive area of the transfer film 28 directly above them. Upon removal of the transfer film 28, the selected cells or sections of tissue are transferred along with the film 28. Because of the small diameter of the laser beam 40, extremely small cell clusters or single cells may be microdissected from a tissue section 36.

After the selective capture of tissue is performed and target cells transferred to the transfer film 28, it is desired to bring the transfer film 28 with the captured cells in contact with fluids in order to extract certain biomolecules, such as DNA, RNA, or proteins from selected sections of the film 28. A small amount of fluid, less than approximately 20 microliters, is oftentimes desirable. Even smaller quantities are desired, for example, in single cell extractions. The extraction device 10 of the present invention facilitates the extraction process by providing a reservoir to contain fluids in contact with transfer film 28 and extract desired biomolecules from the transfer film 28.

Referring now to FIGS. 1, 5-8, the extraction device 14 includes a carrier-receiving portion 42, a first end 44, a second end 46, an inner surface 48, and an outer surface 50. The outer surface includes an outwardly extending shoulder 52 that is substantially circular in shape and includes a plurality of notches 54. The notches 54 enable the extraction device 14 to be handled more easily. The extraction device 14 is made from a rigid polymer such as acrylic or polycarbonate, a flexible polymer such as polyethylene or Tefzel® (Tefzel® is a registered trademark of E. I. du Pont de Nemours & Co. in Wilmington, Del.), a rubber such as silicone, a closed cell foam, glass or ceramic material.

As shown in FIGS. 1, 5-8, the carrier-receiving portion 42 at the first end 44 has a shape that is generally complementary to the carrier 12 that is received within the extraction device 14. In one variation, the carrier-receiving portion 42 includes at least one flange. Four flanges 56 projecting from the shoulder 52 are shown in FIGS. 1, 5-8. The flanges 56 are slightly curved to collectively substantially encompass and to receive a lower portion 20 of the carrier 12. Each of the flanges 56 includes an inner surface 58, an outer surface 60, and a rim 62. The rim 62 includes a beveled surface 64 for guiding the insertion of the lower portion 20 of the carrier 12.

In one embodiment, the extraction device 14 includes securing features (not shown) such that the carrier 12 is secured to the extraction device 14 via the securing features when the carrier 12 is received in the extraction device 14 at the first end 44. Various securing features are employed. For example, as shown in FIGS. 1, 5-8, the flanges 56 exert a force normal to their inner surfaces 58 in a compression-fit engagement when the carrier 12 is inserted into the carrier-receiving portion 42. Alternatively, securing features to create a snap-fit engagement are formed in the carrier-receiving portion 42 and/or the carrier 12. In another alternative, securing features to create a lock-and-key fit engagement are formed in the carrier-receiving portion 42 and/or the carrier 12. In yet another alternative, securing features include adhesive to secure the carrier to the extraction device 14.

Figure 6:
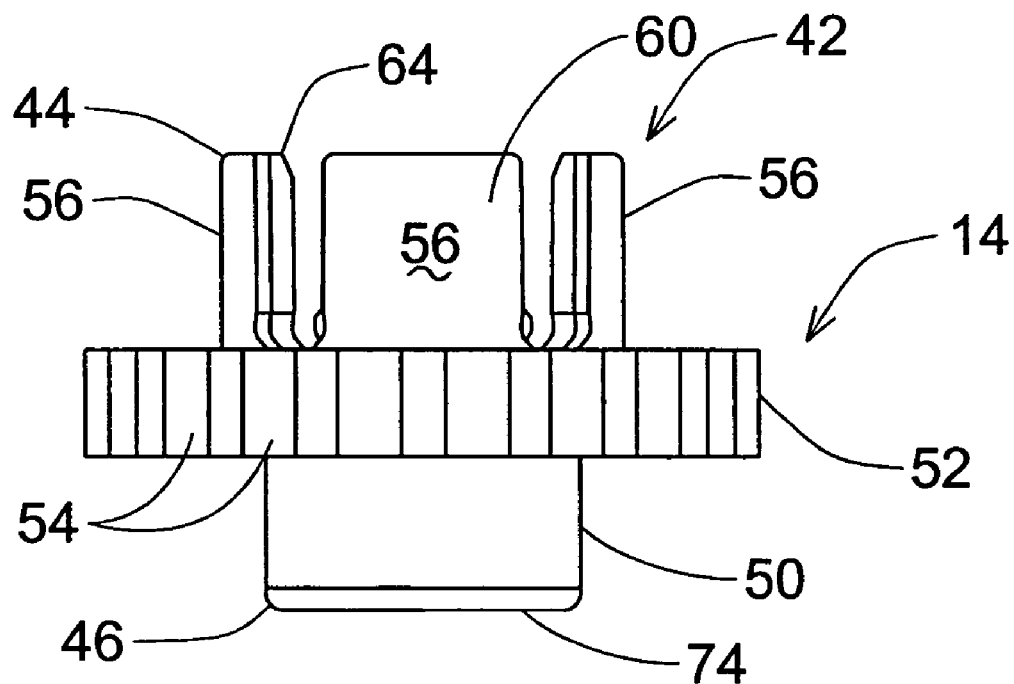
FIG. 6 is a side view of an extraction device of the present invention.
Figure 7:
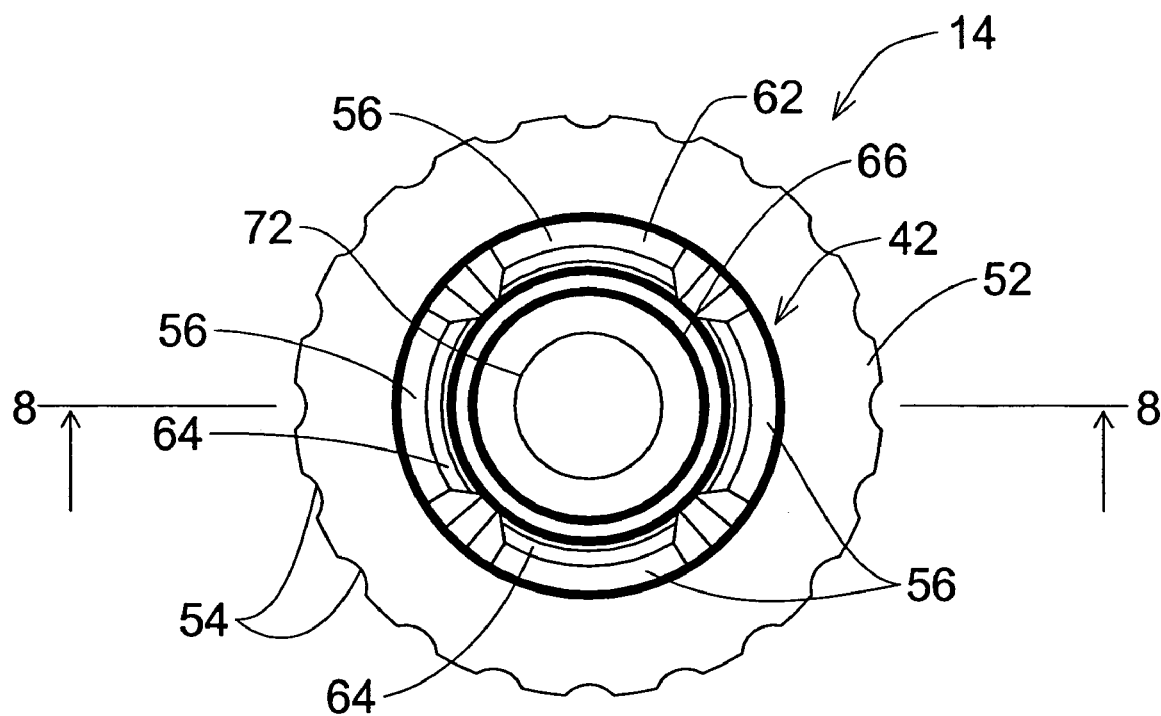
FIG. 7 is a top view of an extraction device of the present invention.
Figure 8:
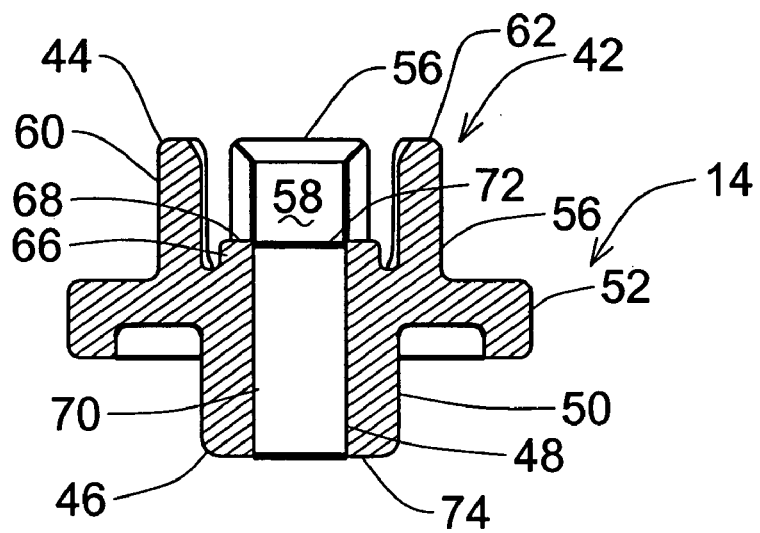
FIG. 8 is a cross-sectional view along line 8-8 of FIG. 7 of an extraction device of the present invention.

The carrier-receiving portion 42 further includes a landing portion 66 having a landing surface 68. As shown in FIGS. 4, 6, and 8, the landing portion 66 extends above the shoulder 52. The landing portion 66 is raised above the shoulder 52 to generate a force response upon the inserted carrier 12 such that the carrier 12 is retained in a compression-fit within the extraction device 14 under mechanical and thermal strains that may be encountered during the extraction process.

The extraction device 14 further includes at least one conduit 70. An inner opening 72 to the conduit 70 is defined in the landing surface 68 and the conduit 70 extends between the landing portion 66 and the second end 46 of the extraction device 14. Although a cylindrically-shaped conduit 70 and a circular inner opening 72 are depicted the inner opening 72 and the conduit 70 may be of any shape. The second end 46 includes a rim 74. In one embodiment, the extraction device 14 includes mating features (not shown) generally located at the second end 46 for mating with a vessel such as a centrifuge tube or a microtiter plate.

Focusing now on FIG. 1, the gasket 16 includes a first surface 76 and a second surface 78. An aperture 80 is defined in the gasket 16. The gasket 16 is overlaid onto the landing portion 66 such that the gasket 16 is located between the carrier 12 and the extraction device 14 and the aperture 80 is aligned with the inner opening 72.

Figure 9:
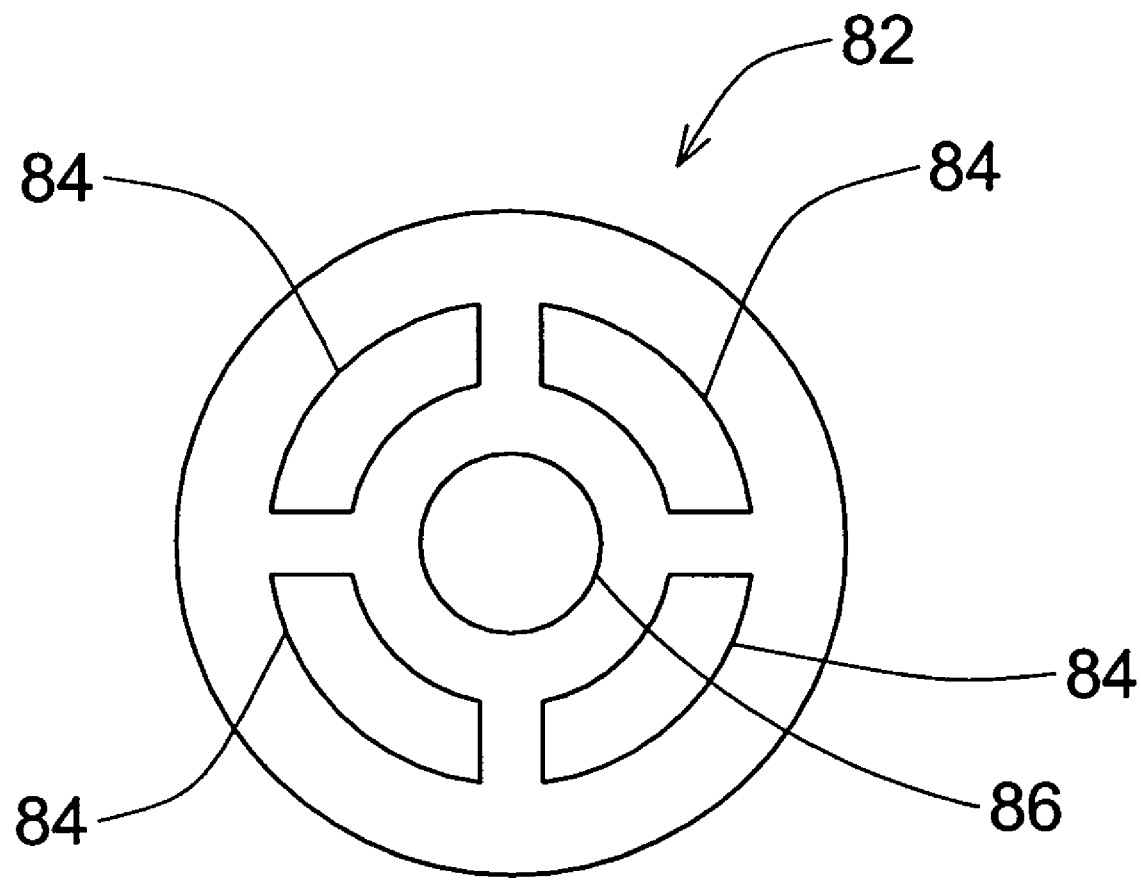
FIG. 9 is a top view of a gasket of the present invention.

FIG. 9 depicts a top view of another variation of a gasket 82. As shown in FIG. 9, four apertures 84 are defined in the gasket 82 for receiving the four flanges 56 of the carrier-receiving portion 42. The gasket 82 also defines a central aperture 86 that corresponds to the inner opening 72 of the extraction device 14. To position the gasket 82, the flanges 56 are passed through the apertures 84. Since the apertures 84 have a shape corresponding to the shape of the flanges 56, the gasket 82 is held in position such that the central aperture 86 is aligned with the inner opening 72 and the gasket 82 contacts the landing surface 68.

The gasket 16, 82 assists in sealing the carrier 12 to the extraction device. The gasket 16, 82 is made of a sealing material such as a conformable polymer, elastomer, rubber, or a pressure sensitive adhesive. The pressure sensitive adhesive is selected to bond under moderate temperature and pressure conditions, such as room temperature and atmospheric pressure and to remain bonded throughout the fluid treatment that could involve mechanical strains and elevated temperatures of approximately 20-50° C. An example of a pressure sensitive adhesive is #8141 from Minnesota Mining & Manufacturing Co. in St. Paul, Minn. Silicone rubber with hardness values in the range of 10-100 Shore A are also useful. The gasket 16, 82 may be integrally formed with the extraction device 14. Alternatively, features, such as ridges or ribs (not shown) on the landing surface 68 are formed to seal the inner opening 72.

Figure 10A:
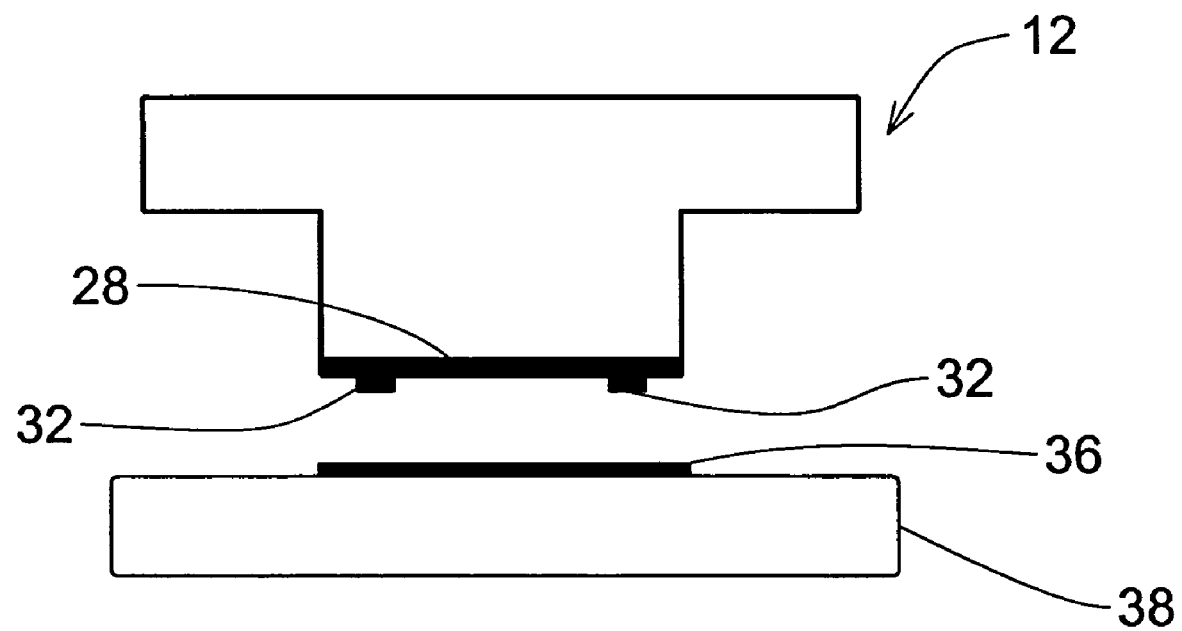
FIG. 10A-10E is a sequence of operation of the present invention.
Figure 10B:
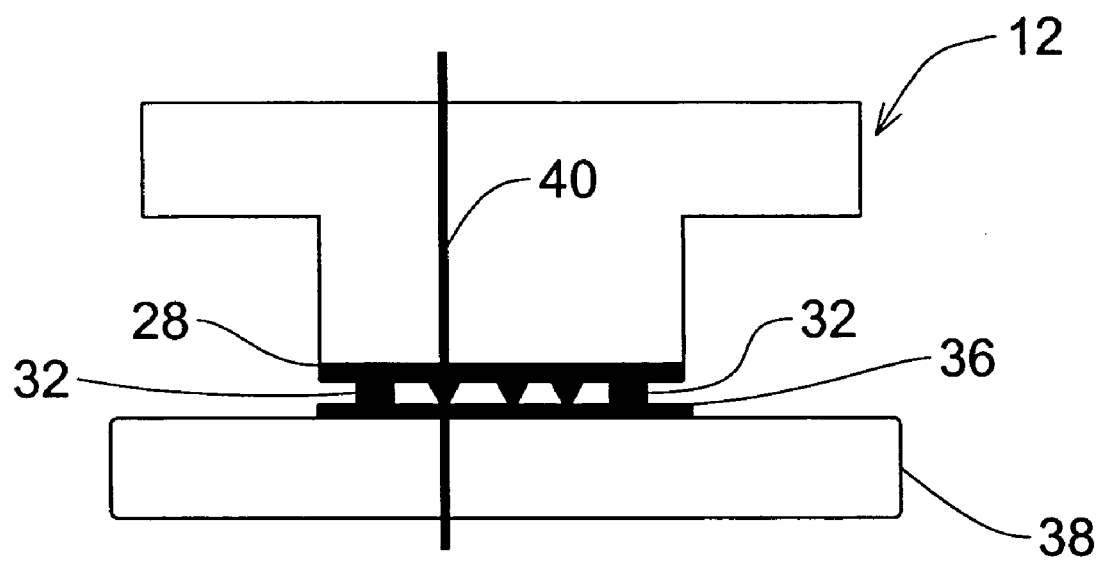

Referring now to FIGS. 10A-10E, there is shown a sequence of operation. In FIGS. 10A and 10B, a carrier 12 having stand-off portions 32 is lowered and positioned over a glass slide 38 and a tissue sample 36 such that the stand-off portions 32 contact the tissue sample 36 and space the transfer film 28 away from the tissue sample 36. Alternatively, the transfer film 28 is not spaced from the tissue sample 36 and the transfer film 28 contacts the tissue sample 36 prior to activation by the laser pulse 40. The carrier 12 is easily handled, either manually or by automated means such as an LCM apparatus of the kind disclosed in the following co-pending applications: U.S. Ser. No. 09/018,452 filed Feb. 4, 1998, U.S. Ser. No. 09/121,691 filed on Jul. 23, 1998, U.S.

Ser. No. 09/121,635 filed on Jul. 23, 1998, U.S. Ser. No. 09/058,711 filed on Apr. 10, 1998, U.S. Ser. No. 09/121,677 filed on Jul. 23, 1998, U.S. Ser. No. 09/208,604 filed on Dec. 8, 1998, and U.S. Ser. No. 09/617,742 filed on Jul. 17, 2000.

Next, the tissue sample 36 is inspected using a microscope (not shown) until a desired cell or cells are targeted. Then, as shown in FIG. 10B, the laser is activated and the laser pulse, shown diagrammatically at reference numeral 40, is directed to at least one target location activating the portion of the transfer film 28 located above the target cell or cells. The transfer film 28 is activated to absorb energy from the laser such that a selected portion of the transfer film 28 expands to contact the tissue 36 and cause adhesion of the target cells 88 to the transfer film 28. The laser is activated one or more times to capture one or more cells. Mechanical adhesion of the cell or cells occurs as interlocking occurs when, due to heating, the thermoplastic material flows about and into the voids of the rough tissue sample surface and interlocks upon subsequent cooling. Alternatively, adhesion occurs as the expanding transfer film 28 contacts the selected area such that it adheres to the transfer film 28.

Figure 10C:
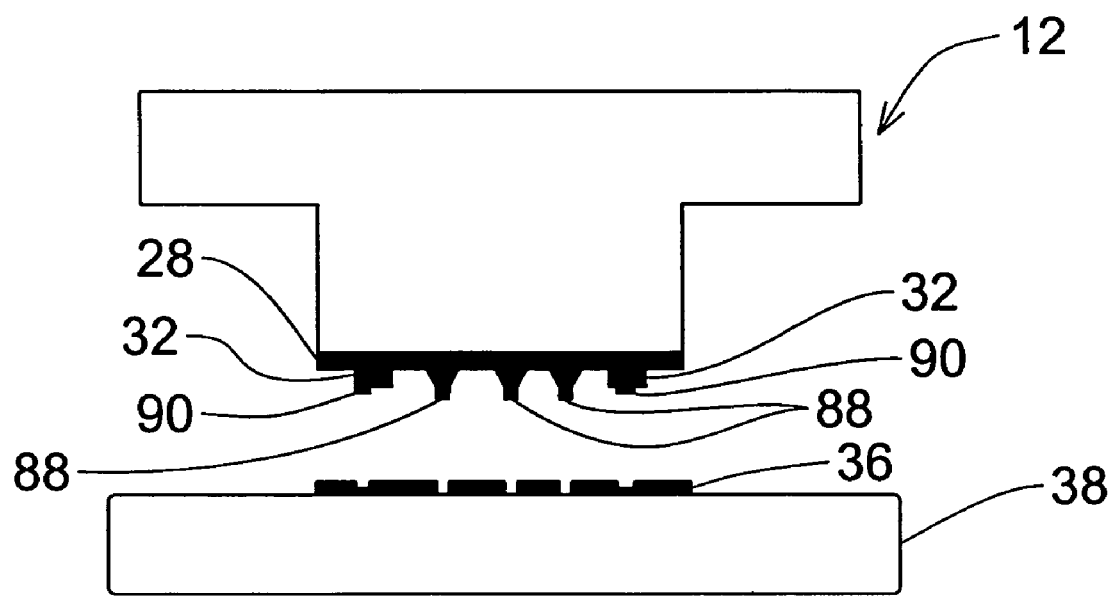

After the activated portion or portions of the transfer film 28 substantially solidify, the transfer film 28 is withdrawn as the carrier 12 is lifted away from the tissue sample 36 as shown in FIG. 10C. The physical interface between the transfer film 28 and the selected area(s) 88 of the tissue sample 36 intended for microdissection causes the transfer film 28 when it is withdrawn to "pull" the target cells 88 from the remainder of the specimen 36. Micro-capture of the target matter occurs.

When the carrier 12 is lifted away from the tissue sample 36, non-specific transfer of unwanted biomolecules or other matter 90 is shown to occur at the stand-off portions 32. Loosely attached or friable unwanted tissue or other material 90 is adhered to the points of contact, in particular, the stand-offs 32, when the carrier 12 is removed. The stand-offs 32 advantageously confine the non-specific transfer of unwanted biomolecules 90.

Figure 10D:
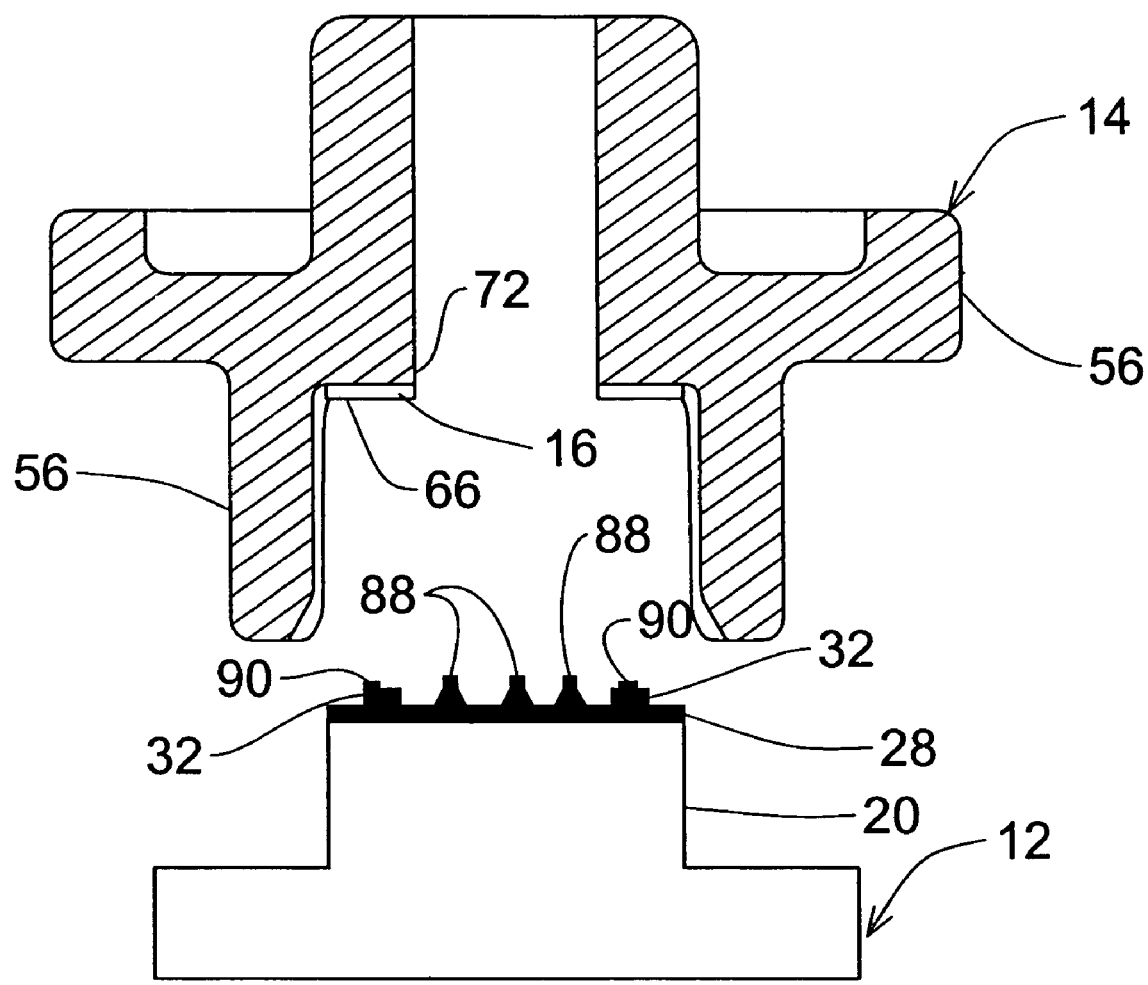
Figure 10E:
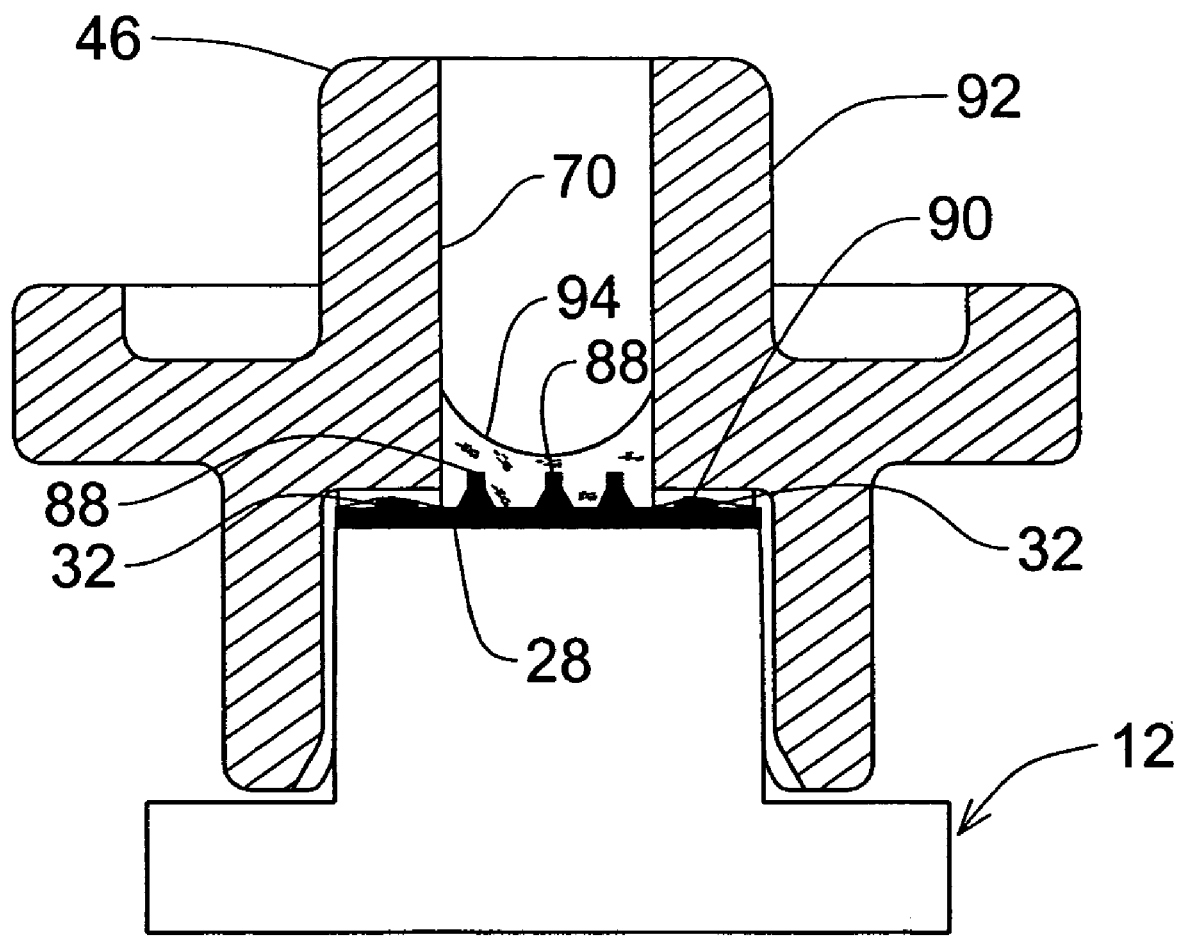

Referring now to FIGS. 10D and 10E, the carrier 12 and the extraction device 14 are engaged to form an extraction system. The lower portion 20 of the carrier 12 is passed between the flanges 56. Under force from the carrier 12, the flanges 56 are slightly outwardly deflected to exert a compressive force onto the lower portion 20 of the carrier 12. Hence, when in position, the carrier 12 is secured to the extraction device 14 in a compression-fit engagement. Alternatively, other securing features of the type discussed above are employed.

When inserting the carrier 12 into the extraction device 14, the carrier 12 is passed into the extraction device until the carrier 12 contacts the gasket 16 located on the landing portion 66. The stand-offs 32 contact the gasket 16 such that the unwanted material 90 attached thereto does not enter the inner opening 72. The transfer film 28 closes the inner opening 72 forming a reservoir 92 with the conduit 70. Hence, the transfer film 28 with the adhered targeted material 88 within the adhesion zone 34 is disposed within the reservoir 92 for subsequent analysis. The remaining portion of the transfer film is disposed outside the reservoir 92. Extraction fluid 94 is then provided into the reservoir 92 via the second end 46 and contained as shown in FIG. 10E. Extraction of selective biomolecules, such as DNA, RNA, or proteins, proceeds in accordance with any number of extraction protocols known to a person skilled in the art.

The extraction system 10 advantageously and selectively shields unwanted biomolecules 90 from entry into the reservoir 92. Since the unwanted biomolecules 90 are first confined to the stand-offs 32 and then selectively brought into contact with the gasket 16, 82 or covered by the landing portion 66, contamination is prevented as fluid 94 is unable to contact the unwanted material 90 on the stand-offs 32 as a seal or a fluidic barrier is formed such that fluid is retained in the reservoir 92. In the variation without stand-offs, contamination is likewise prevented as unwanted biomolecules 90 that are adhered to portions of the transfer film 28 are brought into contact with the gasket 16, 82 or covered by the landing portion 66 to form a fluidic barrier.

Figure 11:
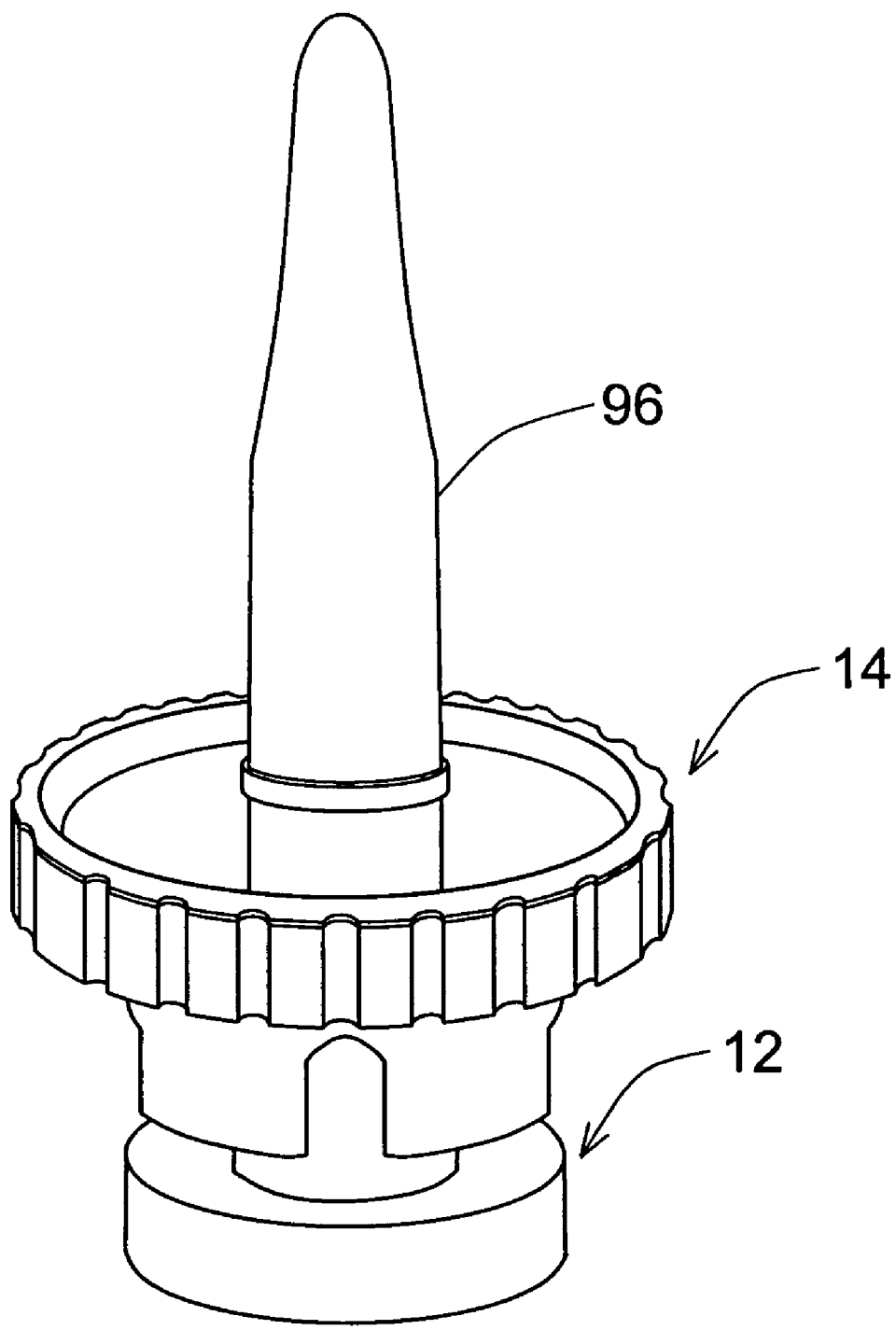
FIG. 11 is an extraction system coupled to a vessel of the present invention.

In one embodiment, the second end 46 is covered to minimize evaporation of the extraction fluids 94 during the extraction process or other processes. Hence, the reservoir 92 may be covered or uncovered. In one embodiment, the cover (not shown) is a flat sheet that is adhered to the rim 74 covering the second end 46. In another embodiment, a vessel 96 such as a centrifuge tube is coupled to the extraction device 14 at the second end 46 as shown in FIG. 11. Alternatively, a microtiter plate (not shown) is coupled to the conduit 70 of the extraction device 14. Securing features of the type discussed above may also be formed in the extraction device 14 and/or the vessel 96 to secure the vessel 96 to the extraction device 14.

The extraction system 10 advantageously enables transfer of the contents of the reservoir 92 to another vessel 96, such as a centrifuge tube, by centrifugation, thereby, minimizing sample handling. Although the drawings show a single conduit 70 in the extraction device 14 mating with a single adhesion zone 34, the invention is not so limited. Multiple adhesion zones 34 on the carrier 12 mating with multiple conduits 70 in the extraction device 14 to form multiple reservoirs 92 and hence, multiple locales for processing fluid on the transfer film are within the scope of the invention. In one embodiment, the extraction system 10 involves mating with a 96-well, 384-well or other standard plate.

Referring now to FIGS. 12-15, an extraction device 100 of another embodiment is depicted. The extraction device 100 includes a carrier-receiving portion 102, first end 104, a second end 106, an inner surface 108, and an outer surface 110. The outer surface 110 includes an outwardly extending shoulder 112. The extraction device 100 is made from a rigid polymer such as acrylic or polycarbonate, a flexible polymer such as polyethylene or Tefzel® (Tefzel® is a registered trademark of E. I. du Pont de Nemours & Co. in Wilmington, Del.), a rubber such as silicone, a closed cell foam, glass or ceramic material.

Figure 12:
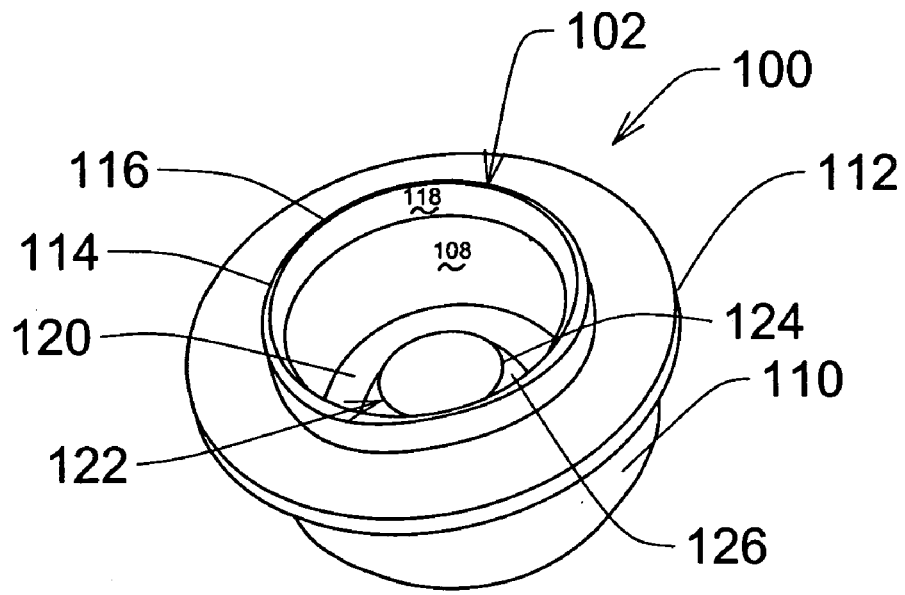
FIG. 12 is a perspective view of an extraction device of the present invention.
Figure 13:
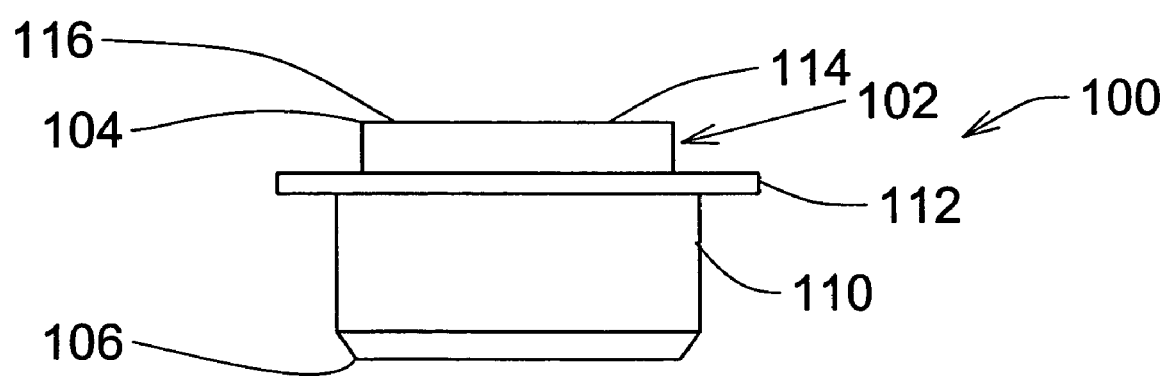
FIG. 13 is a side view of an extraction device of the present invention.
Figure 14:
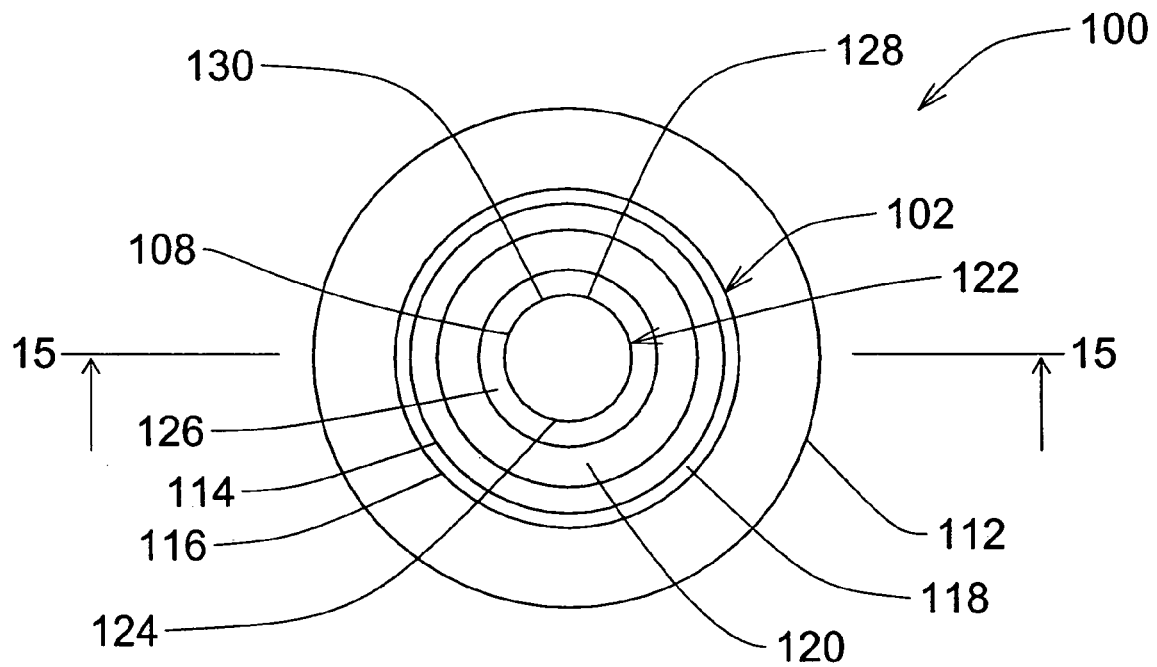
FIG. 14 is a top view of an extraction device of the present invention.

As shown in FIGS. 12-15, the carrier-receiving portion 102 at the first end 104 has a shape that is generally complementary to the carrier 12 that is received within the extraction device 100. For example, as seen in FIG. 12, the inner surface 108 is substantially cylindrical in shape for receiving a lower portion 20 of the carrier 12. The carrier-receiving portion 102 defines an opening 114 that is encompassed by a carrier-receiving rim 116. The carrier-receiving rim 116 includes a beveled surface 18 such that the opening 114 narrows with distance towards the second end 106. The beveled surface 118 guides a carrier 12 as it is being inserted into the opening 114. The inner surface 108 of the carrier-receiving portion 102 is adapted to conform to the shape of the carrier 12 that is receiving in the opening 114.

In one embodiment, the extraction device 100 includes securing features (not shown) such that the carrier 12 is secured to the extraction device 100 via the securing features when the carrier 12 is received at the first end 104. Various securing features are employed. For example, the inner surface 108 of the carrier-receiving portion 102 is designed to exert a force normal to the inner surface 102 such that a compression-fit engagement is formed when the carrier 12 is inserted into the carrier-receiving portion 102. Alternatively, securing features to create a snap-fit engagement are formed in the carrier-receiving portion 102 and/or the carrier 12. In another alternative, securing features to create a lock-and-key fit engagement are formed in the carrier-receiving portion 102 and/or the carrier 12. In yet another alternative, securing features include adhesive, for example, on the inner surface 108 to secure the carrier 12 to the extraction device 100.

The carrier-receiving portion 102 further includes a recess 120 and a landing portion 122. The landing portion 122 includes a landing surface or rim 124 that is raised with respect to the recess 120 and is interconnected therewith via a side surface 126. As shown, the side surface 126 is angled with respect to the recess 120 such that the landing surface 124 forms a pointed edge.

Figure 15:
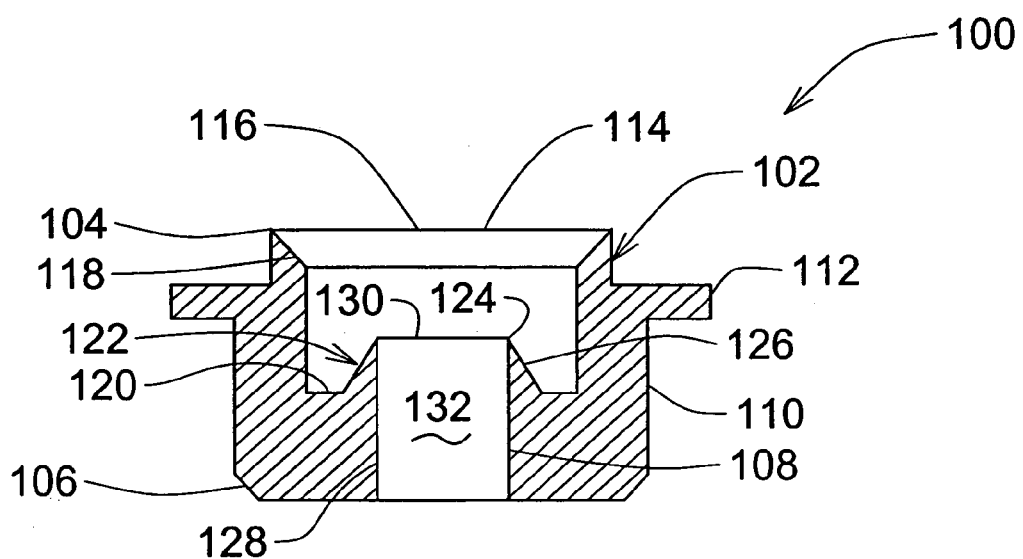
FIG. 15 is a cross-sectional view along line 15-15 of FIG. 14 of an extraction device of the present invention.

The extraction device 100 further includes at least one conduit 128. An inner opening 130 to the conduit 128 is defined by the landing rim 124 and the conduit 128 extends between the landing rim 124 and the second end 106 of the extraction device 100. As shown in FIG. 15, the inner opening 130 is cylindrical in shape and has a diameter that is smaller than the diameter of opening 114. Although a cylindrically-shaped conduit 128 and a circular inner opening 130 are depicted, the inner opening 130 and the conduit 128 may be of any shape. In one embodiment, mating features (not shown) are formed at the second end 106 of the extraction device 100 for mating with a vessel 96 such as a centrifuge tube or a microtiter plate.

When a carrier 12 of the type described with respect to FIGS. 1-3 is inserted into the extraction device 100 to form an extraction system. The carrier 12 is passed into the carrier-receiving portion 102 until the carrier 12 contacts the landing rim 124. As the carrier 12 is inserted into the carrier-receiving portion 102, hoop stresses are generated such that forces normal to the inner surface 108 hold the carrier 12 within the extraction device 100. When the landing rim 124 contacts the carrier 12, the landing rim 124 impresses upon the transfer film 28 such that the sharp-edged landing rim 124 seals against the carrier 12 and keeps the stand-offs 32 and the unwanted biomolecules 90 attached thereto outside of the inner opening 130. With sufficient force, the landing rim 124 will cut into the transfer film 28 to create a seal or fluidic barrier. The transfer film 28 of the carrier 12 closes the inner opening 130 to form a reservoir 132 with the conduit 128. Hence, a portion of the transfer film 28 with the adhered targeted material 88 is disposed within the reservoir 132 for subsequent analysis and a remaining portion is selectively disposed outside the reservoir. Extraction fluid is then provided into the reservoir 132 at the second end 106 and contained such that the seal created by the landing rim 124 against the carrier 12 provides a fluidic barrier during the introduction of fluids and during subsequent analysis.

The extraction system advantageously shields unwanted matter 90 from entry into the reservoir 132. Since the unwanted matter 90 is first confined to the stand-offs 32 and then sealed away from the inner opening 130, contamination is prevented as fluids that are introduced into the reservoir 132 are unable to contact the unwanted material 90 on the stand-offs 32. In the variation without stand-offs 32, contamination is likewise prevented as unwanted biomolecules 90 that are adhered to portions of the transfer film 28 are brought into contact with the landing portion 122 and/or gasket.

In one embodiment, the second end 106 is covered to minimize evaporation of the extraction fluids during the extraction process or other processes. Hence, the reservoir 132 may be covered or uncovered. In one embodiment, the cover (not shown) is a flat sheet that is adhered to the second end 106. In another embodiment, a vessel such as a centrifuge tube is coupled to the second end 106 of the extraction device. Alternatively, a microtiter plate (not shown) is coupled to the extraction device. Securing features of the type described above may also be formed in the extraction device 100 and/or the vessel to secure the vessel to the extraction device 100.

The extraction system advantageously enables transfer of the contents of the reservoir 132 to another vessel, such as a centrifuge tube, by centrifugation, thereby, minimizing sample handling. Although the drawings show a single conduit 128 and a single inner opening 132 mating with a single adhesion zone 34, the invention is not so limited. Multiple adhesion zones 34 on the carrier 12 mating with multiple inner openings 130 in the extraction device 100 to form multiple reservoirs 132, and hence, multiple locales for processing fluids on the transfer film are within the scope of the invention. In one embodiment, the extraction system involves mating with a 96-well, 384-well or other standard plate.

Referring now to FIG. 16-20, an extraction device 134 of another embodiment is depicted. The extraction device 134 includes a carrier-receiving portion 136, a first end 138, a second end 140, an inner surface 142, and an outer surface 144. The outer surface 144 includes a shoulder 146. The extraction device 134 is made from a rigid polymer such as acrylic or polycarbonate, a flexible polymer such as polyethylene or Tefzel® (Tefzel® is a registered trademark of E. I. du Pont de Nemours & Co. in Wilmington, Del.), a rubber such as silicone, a closed cell foam, glass or ceramic material.

Figure 16:
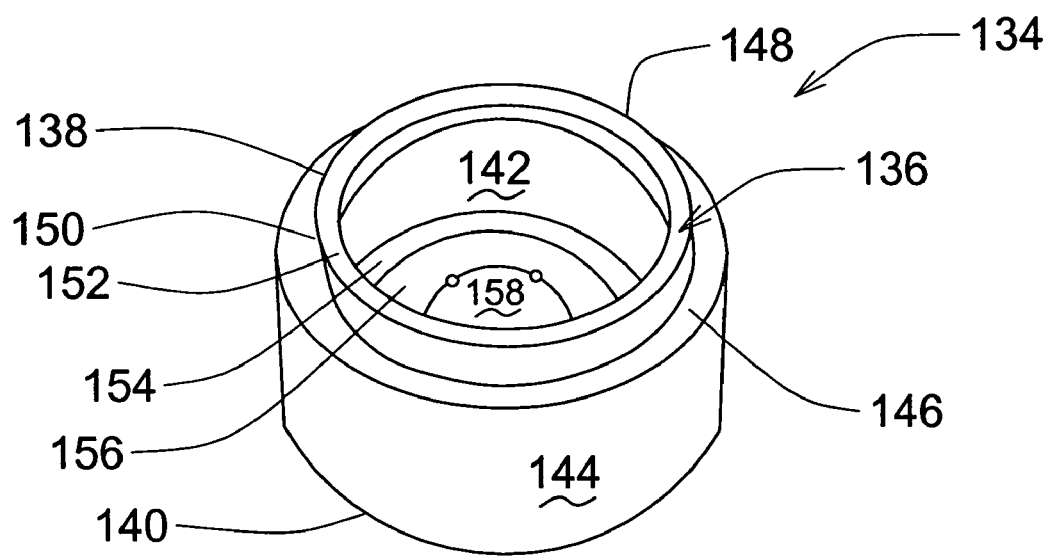
FIG. 16 is a perspective view of an extraction device of the present invention.
Figure 17:
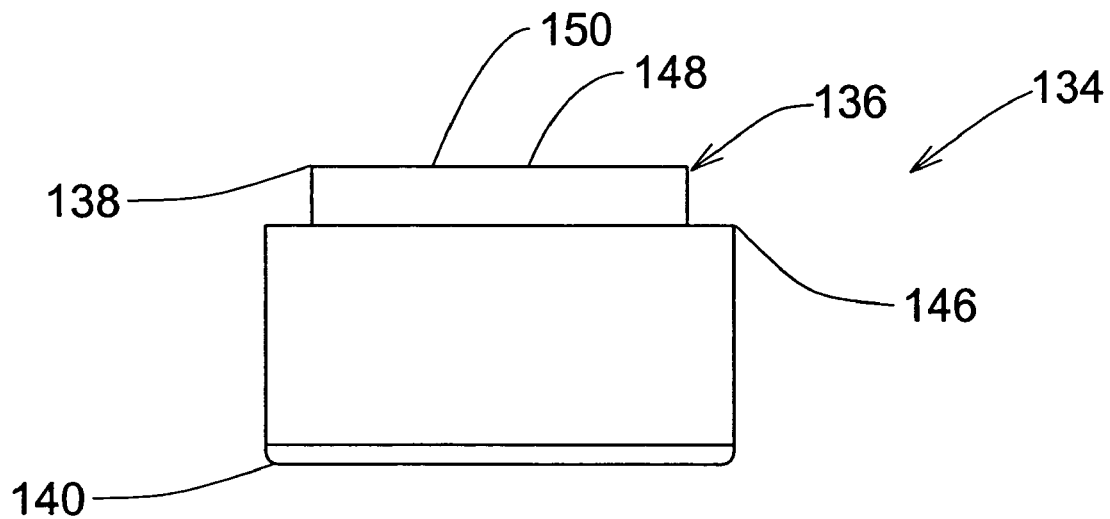
FIG. 17 is a side view of an extraction device of the present invention.
Figure 18:
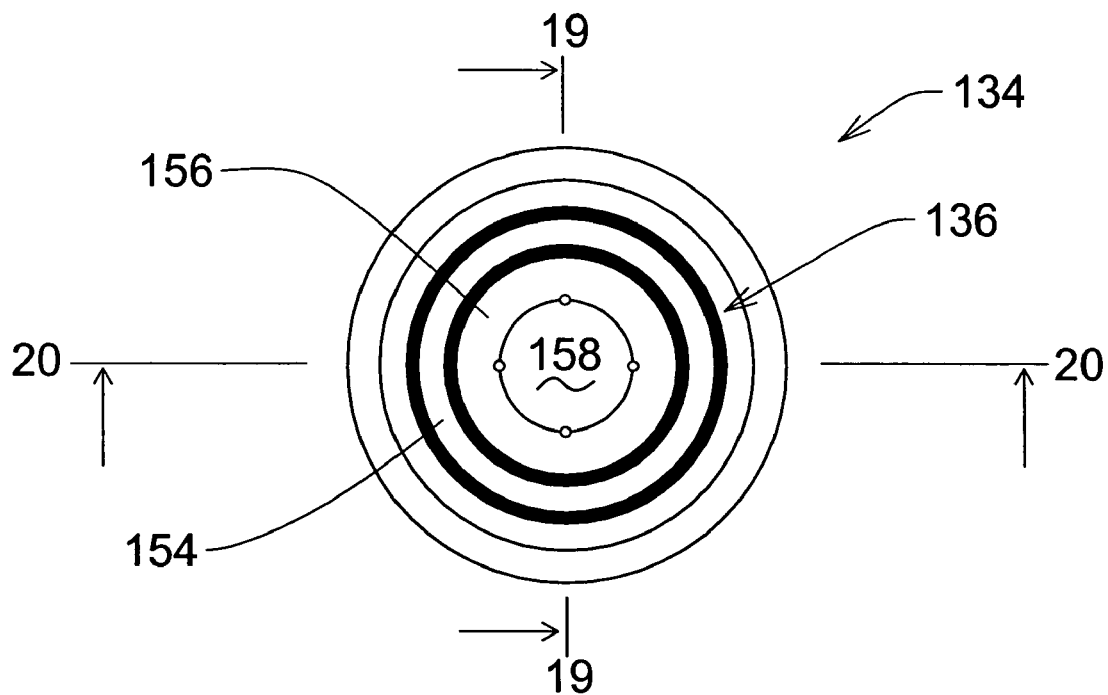
FIG. 18 is a top view of an extraction device of the present invention.

As shown in FIGS. 16-20, the carrier-receiving portion 136 at the first end 138 has a shape that is generally complementary to the carrier 12 that is received within the extraction device 100. For example, as seen in FIG. 16, the carrier-receiving portion 136 is substantially cylindrical in shape for receiving a lower portion 20 of the carrier 12.

In one embodiment, the extraction device 134 includes securing features (not shown) such that the carrier 12 is secured to the extraction device 134 via the securing features when the carrier 12 is received at the first end 138. Various securing features are employed. For example, the inner surface 142 of the carrier-receiving portion 136 is designed to exert a force normal to the inner surface 142 such that a compression-fit engagement is formed when the carrier 12 is inserted into the extraction device 134. Thereby, sufficient force is exerted on the carrier 12 to retain the carrier 12 in the extraction device 134. Alternatively, securing features to create a snap-fit engagement are formed in the carrier-receiving portion 136 and/or the carrier 12. In another alternative, securing features to create a lock-and-key fit engagement are formed in the carrier-receiving portion 136 and/or the carrier 12. In yet another alternative, securing features include adhesive, for example, on the inner surface 142 to secure the carrier 12 to the extraction device 134.

In one embodiment, the carrier-receiving portion 136 includes a rim 148 at the first end 138. The rim 148 encompasses an opening 150 and includes a beveled surface 152 such that the opening 150 narrows with distance towards the second end 140. The beveled surface 152 guides the carrier 12 as it is being inserted into the opening 150.

The carrier-receiving portion 136 includes a recess 154, a landing portion 156, and a reservoir-forming surface 158. The recess is interconnected with the inner surface and the landing portion, the reservoir-forming surface is encompassed by the landing portion. Although a reservoir-forming surface 158 that is generally circular in shape is shown, the invention is not so limited and the reservoir-forming surface 158 may be of any shape. The landing portion 156 is raised from the recess 154 and reservoir-forming surface 158.

Figure 19:
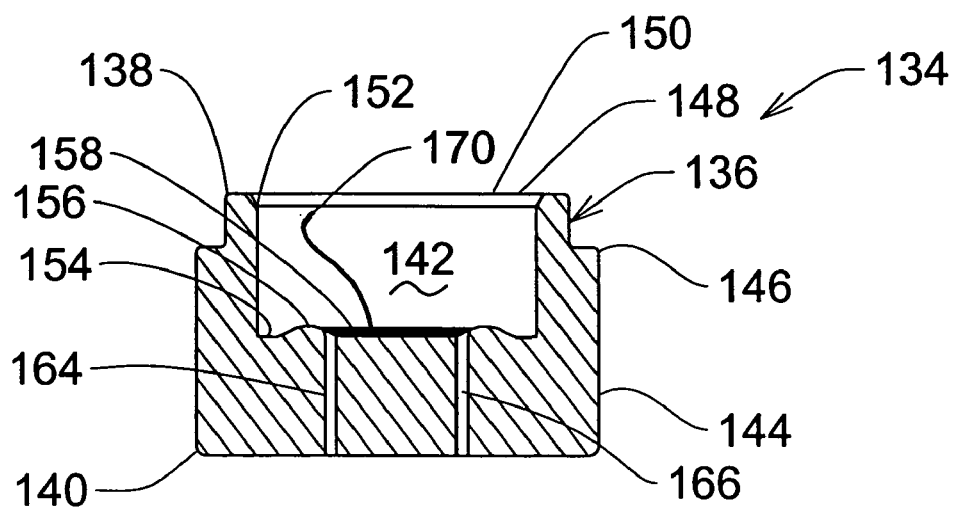
FIG. 19 is a cross-sectional view along line 19-19 of FIG. 18 of an extraction device of the present invention.
Figure 20:
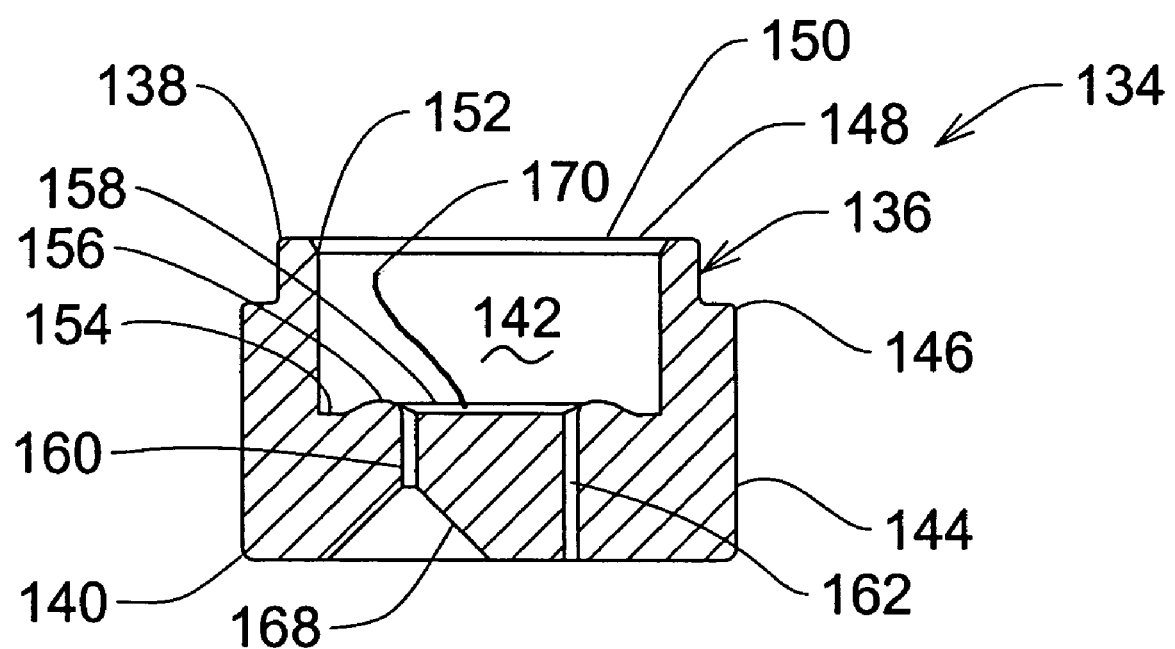
FIG. 20 is a cross-sectional view along line 20-20 of FIG. 18 of an extraction device of the present invention.

As shown in FIGS. 19-20, the extraction device 134 further includes a first conduit 160, a second conduit 162, a third conduit 164, and a fourth conduit 166. The conduits 160, 162, 164, 166 extend from the reservoir-forming surface 158 to the second end 140 of the extraction device 134. Although the conduits 160, 162, 164, 166 are shown to extend to the second end 140, the invention is not so limited. For example, in one embodiment the conduits 160, 162, 164, 166 extend to the outer surface 144. Furthermore, although four conduits 160, 162, 164, 166 are illustrated, the invention is not so limited and any number of conduits is within the scope of the invention. Also, the conduits 160, 162, 164, 166 may be of any shape.

The conduits 160, 162, 164, 166 allow for the introduction and/or removal of fluid, gaseous and/or liquid, at the reservoir-forming surface 158. For example, as shown in FIG. 20, the first fluid conduit 160 includes a beveled surface 168 at the second end 140 for introducing fluid at the reservoir-forming surface 158, for example via a pipette. The second, third, and fourth conduits 162, 164, 168 are used, for example, as exit ports for venting air and/or fluid.

Furthermore, the geometry of the conduits 160, 162, 164, 166 along with the reservoir-forming surface 158 can be tailored to provide a desired filling or flow pattern. For example, fluid may be introduced at one end of the reservoir-forming surface 158 and removed at another end. Also, the conduits 160, 162, 164, 166 are dimensioned for capillarity such that fluid is not removed without force such as when subject to centrifugation. In one embodiment, mating features (not shown) of the type described above are formed for mating with a vessel 96 such as a centrifuge tube or a microtiter plate.

A carrier 12 is inserted into the extraction device 134 to form an extraction system. In one variation, the extraction system includes a gasket of the type described above disposed between the carrier 12 and the extraction device 134. The carrier 12 is passed into the carrier-receiving portion 136 until the carrier contacts the landing portion 156 such that a reservoir 170 is formed. The reservoir 170 is bounded by the carrier 12 with the transfer film 28 at one end, the landing portion 156, and the reservoir-forming surface 158. The transfer film 28 is spaced from the reservoir-forming surface 158 a distance of approximately 2 to 50 µm. With the carrier 12 in contact with the landing portion 156, a reservoir 170 having a volume of approximately 0.01 to 250 µL is formed. The small reservoir 170 is advantageous for a several reasons. For example, for single cell extractions, the small volume aids in obtaining the right dilution factor. Another advantage is realized in the form of cost savings as a result of using smaller volumes of buffer and other fluids for extraction. In one embodiment, the reservoir 170 exhibits capillarity upon the introduction of fluid.

With the carrier 12 of the typed described with respect to FIGS. 1-3 inserted into the carrier-receiving portion 136, the landing portion 156 seals against the carrier 12 and keeps the stand-offs 32 along with the attached unwanted matter 90 transferred by non-specific transfer outside of the reservoir 170. The desirable targeted material 88 that is adhered to a portion of the transfer film 28 by specific transfer results in being selectively disposed within the reservoir 170. Thus, the extraction system advantageously shields unwanted biomolecules 90 from entering the reservoir 170 whereas unwanted matter 90 disposed on the remaining portion of the transfer film 28 is disposed outside the reservoir 170. Since the unwanted biomolecules 90 are first confined to the stand-offs 32 and then sealed from the reservoir 170, contamination is prevented as fluid that is introduced into the reservoir 170 are unable to come in contact with the unwanted material 90 on the stand-offs 32. In the variation without stand-offs 32, contamination is likewise prevented as unwanted biomolecules 90 that are adhered to portions of the transfer film 28 are excluded from the reservoir 170.

In one embodiment, the second end 140 of the extraction device 134 is covered to minimize evaporation of the extraction fluid during the extraction process or other processes. Hence, the reservoir 70 may be covered or uncovered. In one embodiment, the cover (not shown) is a flat sheet that is adhered to the second end. In another embodiment, a vessel 96 such as a centrifuge tube is coupled to the extraction device at the second end 140. Alternatively, a microtiter plate (not shown) is coupled to the extraction device. Securing features of the type described above may also be formed in the extraction device 134 and/or the vessel 96 to secure the vessel 96 to the extraction device 134.

With the carrier 12 in contact with the landing portion 156, fluid is introduced into the reservoir 170 via the first conduit 160. As fluid enters the reservoir 170, air is displaced and is free to exit via the second, third, and/or fourth conduits 162, 164, 166. The extraction device 134 alone or with its second end 140 covered or, alternatively, coupled to a vessel such as a centrifuge tube or microtiter plate is then incubated at a temperature and period in accordance with any one of a number of extraction protocols. The extraction device 134 and the carrier 12 are designed to withstand temperatures of approximately −20 to 100° C. during incubation. In particular, the securing features are sufficient to withstand thermal and mechanical stresses encountered during incubation. Following incubation, the extraction device 134 is centrifuged to transfer fluid from the reservoir 170.

The extraction system advantageously enables transfer of the contents of the reservoir 170 to another vessel, such as a centrifuge tube, by centrifugation, thereby, minimizing sample handling. Although the drawings show the extraction device mating with a single adhesion zone 34, the invention is not so limited. Multiple adhesion zones 34 on the carrier 12 mating to form multiple reservoirs are within the scope of the invention. In one embodiment, the extraction system 10 involves mating with a 96-well, 384-well or other standard plate.

Figure 21:
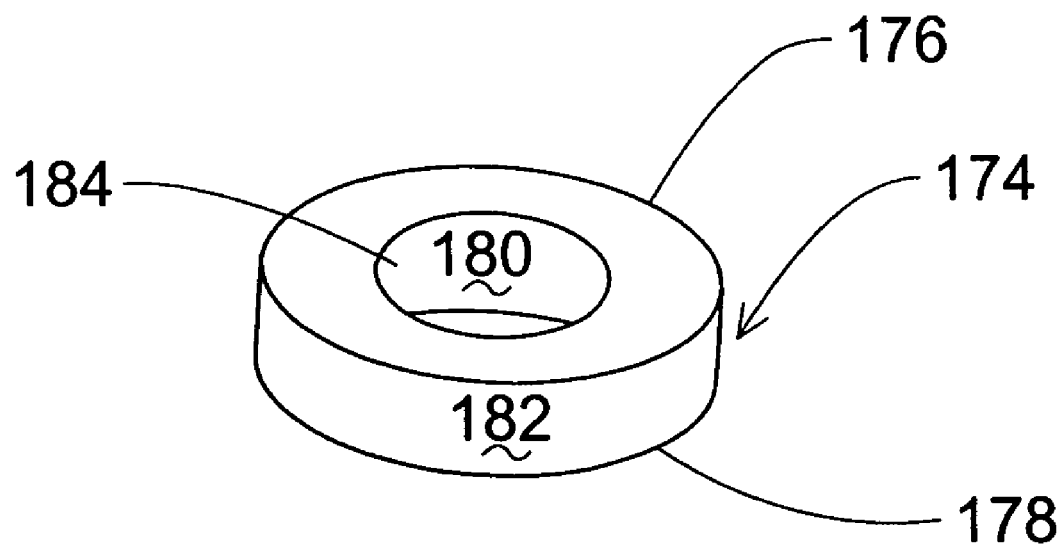
FIG. 21 is a perspective view of an extraction device of the present invention.
Figure 22:
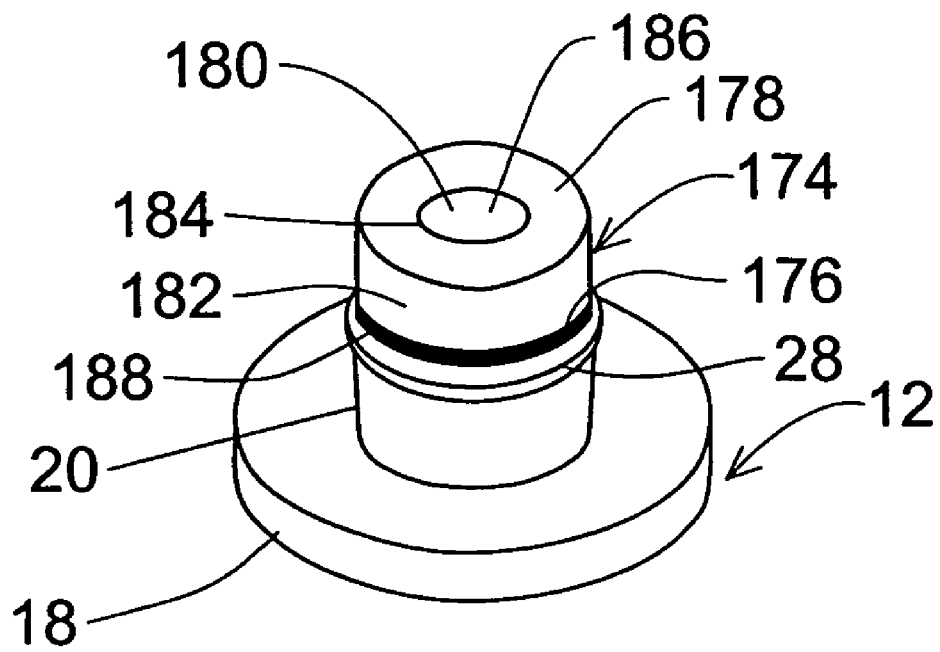
FIG. 22 is a perspective view of an extraction system of the present invention.

Turning now to FIGS. 21-22, there is depicted another embodiment of an extraction device 174 according to the invention. The extraction device 174 includes a first surface 176, a second surface 178, an inner surface 180, and an outer surface 182. The outer surface 182 interconnects the first surface 176 and the second surface 178. Also, the inner surface 180 interconnects the first surface 176 and the second surface 178 to define a conduit 184 between the first surface 176 and the second surface 178. As shown in FIGS. 21 and 22, the extraction device 174 is substantially cylindrical and defines a substantially cylindrical conduit 184. Although, the extraction device 174 and the conduit 184 are shown to be substantially cylindrical, the invention is not so limited and the extraction device 174 and the conduit 184 can be of any shape. Furthermore, although a single conduit 184 is depicted, the invention is not so limited and any number of conduits 184 is within the scope of the invention. The extraction device 174 is made from a rigid polymer such as acrylic or polycarbonate, a flexible polymer such as polyethylene or Tefzel® (Tefzel® is a registered trademark of E. I. du Pont de Nemours & Co. in Wilmington, Del.), a rubber such as silicone, a closed cell foam, glass or ceramic material.

The first surface 176 is at least partially covered with an adhesive material 188 such as a pressure sensitive adhesive ("PSA") for adhering the extraction device 174 to the carrier 12 as shown in FIG. 22. It is desirable to have the adhesive bond form under moderate temperature and pressure conditions, and for the surfaces to remain bonded throughout the extraction protocol and fluid treatment(s), which could involve elevated temperatures and mechanical strains. One example of an adhesive 188 is #8141 from Minnesota Mining & Manufacturing Co. in St. Paul, Minn., which works well for the extraction of DNA from cells with GITC or Proteinase K extraction buffers at temperatures of approximately 42 C. In one embodiment, the second surface 178 is also at least partially covered with an adhesive for adhering the extraction device 174 to a base of a packaging assembly, for example, that is discussed in detail below.

The general operation of extraction device 174 will now be discussed. First, microcapture of desired cells is performed such that the desired captures are located substantially in the central portion of the transfer film 28 which generally corresponds to the location and area of the transfer film 28 that is encompassed by the conduit 184 of the extraction device 174. For example, if the extraction device 174 defines a cylindrical conduit 184 having a diameter, microdissection is performed such that all desired specific captures are made within the diameter of the conduit 184 of the extraction device 174. If multiple conduits 184 are defined within the extraction device 174, multiple captures are located to correspond within the location of such conduits such that material transferred to the transfer film 28 is selectively disposed within the appropriate reservoirs that are formed when the transfer film 28 engages the extraction device 174.

After microcapture, the extraction device 174 is adhered to the carrier 12 such that the first surface 176 contacts the transfer film 28 to form a reservoir 186 and an extraction system. Force may be applied to wet out the adhesive. As shown in FIG. 22, the substantially cylindrically shaped extraction device 174 includes an outer diameter that is substantially the same as the diameter of lower portion 20 of the carrier 12 such that alignment of the extraction device 174 and its adhesion to the carrier 12 is facilitated. Since microcapture was performed such that target cells were contained within a central area or adhesion zone 34 of the transfer film 28 and the extraction device 174 adhered to the transfer film 28 such that the adhesion zone 34 is aligned with the conduit 184 of the extraction device 174, any cells that were transferred to the transfer film 28 and located outside of the adhesion zone 34, as a result of non-specific transfer, for example, are effectively covered up by the first surface 176 of the extraction device 174. With the extraction device 174 secured to the carrier 12, a reservoir 186, that is defined by the transfer film 28 and the inner surface 180 of the extraction device 174, is formed.

The reservoir 186 is small and advantageously provides a locale for processing fluid on the transfer film 28. The reservoir 186 has a volume, for example, less than approximately 30 microliters that keeps the molecules of interest at a high concentration relative to a reservoir of greater volume. In some cases, such as single-cell microcapture, it is desirable to use fluid volumes of less than approximately 0.01 to 250 microliters which is advantageously enabled by the reservoir 186 of the extraction device 174.

Next, extraction fluid, such as buffer, for example, can be disposed within the reservoir 186 such that the fluid contacts the desired target cells for extraction. Because cells that are adhered to a remaining portion of the transfer film 28 in a location outside of the adhesion zone 34 are covered up by the extraction device 174, fluid that enters the reservoir 186 is blocked from contact with the remaining portion of the transfer film 28 covered by the first surface 176. Therefore, any matter that is adhered to the remaining portion that is covered by the first surface 176 is not contacted with fluid and, hence, not extracted. The unwanted matter inadvertently adhered to the transfer film 28 can interfere with the analysis if it comes in contact with the extraction fluid. Therefore, the extraction device 174 advantageously substantially excludes unwanted matter from the reservoir 186 and hence, from digestion by extraction fluids.

The extraction device can be employed with either contact or non-contact LCM. With non-contact LCM, the transfer film 28 is spaced from the sample to prevent non-specific transfer of material. The extraction device is particularly useful in non-contact LCM wherein the transfer film 28 is spaced from the sample using stand-off portions 32. It is the stand-off portions 32 that contact the sample and therefore, unwanted material is generally concentrated only on the stand-off portions 32. The extraction device is designed such it covers at least the stand-off portions 32 carrying the unwanted material and thereby prevents contamination of the analysis.

Figure 23:
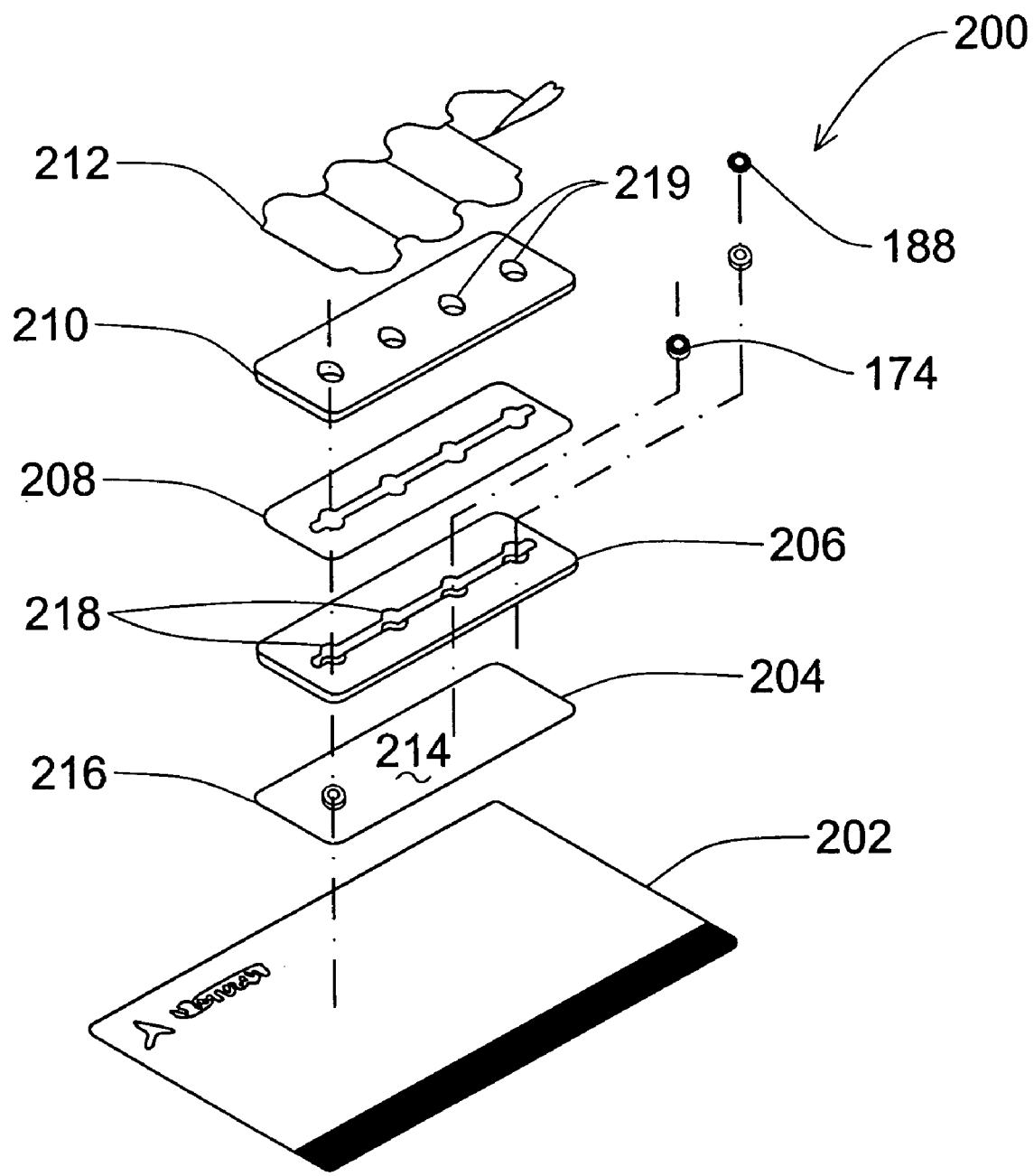
FIG. 23 is an exploded view of an extraction device delivery system of the present invention.

Turning now to FIG. 23, there is shown an extraction device delivery system 200 for use with the extraction device described with respect to FIGS. 21-22. The delivery system 210 includes a base 202, a first adhesive layer 204, a locator 206, a second adhesive layer 208, a guide 210, and a cover 212. The first adhesive layer 204 is located between the locator 206 and base 202. The second adhesive layer 208 is located between the locator 206 and the guide 210 and the protective cover 212 is located above the carrier guide 210. In one variation, the second adhesive layer 208, and guide 210 are omitted and the cover 212 is adhered to the locator 218.

The base 202, which forms the bottom layer of the laminate construction of the delivery system 200, can be made of paper or plastic, for example. The first adhesive layer 204 includes a first surface 214 and a second surface 216. The locator 206 is fixed to the base 202 via the first adhesive layer 204 such that the locator 206 is adhered to the first surface 214 and the second surface 216 of the first adhesive layer 204 is adhered to the base 202. In one variation, the first adhesive layer 204 is a differential adhesive layer such that at least a portion of the first surface 214 includes a first adhesive that has a lower tack relative to a second adhesive on the second surface 216 that has a higher tack. The higher tack adhesive adheres the first adhesive layer 204 to the base 202. The first adhesive adheres the locator 206 to the first adhesive layer 204 and, thereby, to the base 202.

The locator 206 includes at least one locator aperture 218. FIG. 23 shows the locator 206 having four apertures that are interconnected; however, the invention is not so limited and any number of apertures 218 may be formed in the locator 206 and be either interconnected with each other or not. Each of the locator apertures 218 is generally the same shape as the extraction device received in the aperture 218. For example, if the extraction device is cylindrical in shape, a substantially circular aperture 218 is formed in the locator 206. In one variation, the locator 206 has a thickness that is thinner than the overall height of the extraction device. The thinner locator 206 insures that the inserted surface 28 of the carrier 12 contacts the taller upper surface of the device 174, potentially covered with PSA.

Although, the extraction device delivery system 200 is described and illustrated with respect to extraction devices of the type described with respect to FIGS. 21-22, the invention is not limited and the delivery system may be employed with any variation of extraction device. When extraction devices 174 are inserted into the locator apertures 218, the second surface 178 of each extraction device 174 of the type described with respect to FIGS. 21-22, contacts the first surface 214 of the first adhesive layer 204. At least a portion of the first surface 214 of the first adhesive layer 204 carries an adhesive having a tack such that the extraction device 174 is sufficiently retained within the aperture 218 without being inadvertently removable. The delivery system 200 is designed to accommodate and to allow for the insertion and removal of the extraction device 174.

The second adhesive layer 208 fixes the guide 210 to the locator 206. The guide 210 includes at least one guide aperture 219 that is substantially aligned with the at least one locator aperture 218. The guide 210 guides a post-microcapture carrier 12 as it is inserted to contact an extraction device 174. As shown in FIG. 23, the guide 210 and the locator 206 are separate elements. As an alternative, the guide 210 and the locator 206 is a single element fabricated by molding, machining or converting as would be the separate elements adhered together by the second adhesive layer 208.

The protective cover 212 is affixed to the guide 210 to prevent contamination of the extraction device 174 and not to interfere with insertion of the carrier 12. The protective cover 212 is an easily removable layer adhered to the guide 210. The cover 212 can be a tape or other material such as polyester or polycarbonate. As shown in FIG. 23, the cover 212 includes perforations such that the cover 212 is easily and sectionally removable in order to expose one or more extraction devices 174 at a time. In one variation the cover 212 is substantially transparent.

With the extraction device delivery system 200 assembled, a user would first remove the protective cover 212. Then, a post-LCM carrier 12 having targeted material adhered to the transfer film 28 is passed into the guide 210 through the guide aperture 219 such that the lower portion 20 of the carrier 12 with the transfer film 28 is inserted first. The guide 210 guides the carrier 12 until the transfer film 28 contacts an extraction device 174 positioned within the aperture 218 of the locator 206. The extraction device 174 is positioned within the locator aperture 218 such that its first surface 176 is exposed. When the transfer film 28 contacts the first surface 176, the carrier 12 is adhered to the extraction device 174 as a result of the first adhesive 188 on the first surface 176. Sufficient force is applied to carrier to ensure adhesion and wetting of the adhesive 188 to the transfer film 28. As already described, a portion of the transfer film 28 is effectively covered up to prevent exposure of material adhered to the transfer film 28 due to non-specific transfer resulting from the microcapture process. With the carrier 12 adhered to the extraction device 174, the reservoir 186 is formed and the carrier 12 and the extraction device 174 are removed from the extraction device delivery system 200. As the carrier 12 and the extraction device 174 are removed, the extraction device 174 at the second surface 178 is released from the first adhesive layer 204 that held the extraction device 174 to the base 202. As mentioned above, the first adhesive employed on the first surface 214 of the first adhesive layer 204 has sufficient tack to hold the extraction device 174 to the base 202, yet allow removal of the extraction device 174 with ease. When the extraction device 174 and carrier 12 combination is removed from the delivery system 200, the combination is oriented such that the extraction device 174 is connected to the carrier 12 and the reservoir 186 is exposed. Extraction fluid such as buffer can now be disposed within the reservoir 186 and extraction of desired biomolecules commenced.

While the present invention has been described with reference to one or more particular variations, those skilled in the art will recognize that many changes may be made thereto without departing from the spirit and scope of the present invention. Each of these embodiments and obvious variations thereof are contemplated as falling within the spirit and scope of the claimed invention, which is set forth in the following claims.

The invention claimed is:

1. An extraction unit comprising:
   a carrier having an upper portion, a lower portion, and a bottom surface; and
   an extraction device for mating with the carrier having a first end, a second end, an inner surface, and an outer surface, comprising:
      a shoulder that extends outwardly from the outer surface and disposed between the first and second ends;
      a carrier-receiving portion at the first end comprising at least one flange that projects from the shoulder, comprises an inner surface, and is configured to secure the carrier to the extraction device in a compression-fit engagement; and
      a conduit interconnected to the carrier-receiving portion; the conduit extending between a first opening at the carrier-receiving portion and a second opening at the second end;
   wherein the carrier mates with the carrier-receiving portion, closes the first opening, seals the first opening to prevent fluid flow through the bottom surface, and forms a reservoir; wherein the inner surface of the at least one flange contacts the lower portion of the carrier; wherein the second end is adapted to mate with a vessel such that the vessel is in fluid communication with the conduit; and wherein specifically transferred material transferred to the carrier by microdissection and non-specifically transferred material are present on the carrier and some non-specifically transferred material is excluded from the reservoir and some specifically transferred material transferred is included in the reservoir.

2. An extraction unit comprising:
   a carrier having an upper portion, a lower portion, and a bottom surface; and
   a device adapted for mating with the carrier, the device comprising:
      a carrier-receiving portion at a first end comprising at least one flange comprising an inner surface and configured to secure the carrier to the device in a compression-fit engagement;
      a raised landing portion comprising a landing surface adapted to contact the bottom surface and disposed within the carrier-receiving portion; and
      a conduit interconnected to the carrier-receiving portion and extending through the raised landing portion, the conduit having a first opening at the carrier-receiving portion;
   wherein the carrier mates with the device at the carrier-receiving portion and contacts the landing surface to form a reservoir with the bottom surface and at least a portion of the conduit, to close the first opening by the bottom surface and to prevent fluid flow through the first opening; wherein the inner surface of the at least one flange contacts the lower portion of the carrier; wherein the device covers at least a portion of the bottom surface of the carrier from the reservoir; and wherein the bottom surface of the carrier has a non-specifically transferred material and specifically transferred material transferred to the carrier by microdissection and the device covers at least a portion of the non-specifically transferred material and at least a portion of the specifically transferred material is included in the reservoir.

3. An extraction unit comprising:

a carrier having an upper portion, a lower portion, and a bottom surface; and an extraction device for mating with the carrier having a first end, a second end, an inner surface, and an outer surface, comprising:

a shoulder that extends outwardly from the outer surface and disposed between the first and second ends;

a carrier-receiving portion at the first end comprising at least two flanges that each projects from the shoulder, comprises an inner surface, and is configured to secure the carrier to the extraction device in a compression-fit engagement; and a conduit interconnected to the carrier-receiving portion; the conduit extending between a first opening at the carrier-receiving portion and a second opening at the second end; wherein the carrier mates with the carrier-receiving portion, closes the first opening, seals the first opening to prevent fluid flow through the bottom surface, and forms a reservoir; wherein the inner surface of each of the at least two flanges contacts the lower portion of the carrier; and wherein the second end is adapted to mate with a vessel such that the vessel is in fluid communication with the conduit.

4. The extraction unit of claim 3, wherein the carrier-receiving portion comprises at least three flanges that each projects from the shoulder, comprises an inner surface, and is configured to secure the carrier to the extraction device in a compression-fit engagement and wherein the inner surface of each of the at least three flanges contacts the lower portion of the carrier.

5. The extraction unit of claim 3, wherein the carrier-receiving portion comprises four flanges that each projects from the shoulder, comprises an inner surface, and is configured to secure the carrier to the extraction device in a compression-fit engagement and wherein the inner surface of each of the at least four flanges contacts the lower portion of the carrier.

6. An extraction unit comprising:

a carrier having an upper portion, a lower portion, and a bottom surface; and a device adapted for mating with the carrier, the device comprising:

a carrier-receiving portion at a first end comprising at least two flanges that each projects from a shoulder, comprises an inner surface, and is configured to secure the carrier to the extraction device in a compression-fit engagement;

a raised landing portion comprising a landing surface adapted to contact the bottom surface and disposed within the carrier-receiving portion; and a conduit interconnected to the carrier-receiving portion and extending through the raised landing portion, the conduit having a first opening at the carrier-receiving portion;

wherein the carrier mates with the device at the carrier-receiving portion and contacts the landing surface to form a reservoir with the bottom surface and at least a portion of the conduit, to close the first opening by the bottom surface and to prevent fluid flow through the first opening; wherein the inner surface of each of the at least two flanges contacts the lower portion of the carrier; and wherein the device covers at least a portion of the bottom surface of the carrier from the reservoir.

7. The extraction unit of claim 6, wherein the carrier-receiving portion comprises at least three flanges that each projects from the shoulder, comprises an inner surface, and is configured to secure the carrier to the extraction device in a compression-fit engagement and wherein the inner surface of each of the at least three flanges contacts the lower portion of the carrier.

8. The extraction unit of claim 6, wherein the carrier-receiving portion comprises four flanges that each projects from the shoulder, comprises an inner surface, and is configured to secure the carrier to the extraction device in a compression-fit engagement and wherein the inner surface of each of the at least four flanges contacts the lower portion of the carrier.

* * * * *